United States Patent [19]
El-Rashidy et al.

[11] Patent Number: 6,121,276
[45] Date of Patent: Sep. 19, 2000

[54] APOMORPHINE-CONTAINING DOSAGE FORMS FOR AMELIORATING MALE ERECTILE DYSFUNCTION

[75] Inventors: Ragab El-Rashidy, Deerfield; Bruce Ronsen, River Forest, both of Ill.

[73] Assignee: Pentech Pharmaceuticals, Inc., Buffalo Grove, Ill.

[21] Appl. No.: 09/102,406

[22] Filed: Jun. 22, 1998

Related U.S. Application Data

[63] Continuation-in-part of application No. 08/546,498, Oct. 20, 1995, Pat. No. 5,770,606, which is a continuation-in-part of application No. 08/231,250, Apr. 22, 1994, abandoned.

[51] Int. Cl.$^7$ .................................................. A61K 31/44
[52] U.S. Cl. .......................... 514/284; 424/449; 424/464; 424/468; 424/424
[58] Field of Search ........................... 514/284; 424/449, 424/464, 468, 474

[56] References Cited

U.S. PATENT DOCUMENTS

| | | | |
|---|---|---|---|
| 2,818,855 | 1/1958 | Miller | 128/79 |
| 3,976,780 | 8/1976 | Thominet | 424/275 |
| 4,127,118 | 11/1978 | Latorre | 128/79 |
| 4,521,421 | 6/1985 | Foreman | 514/267 |
| 4,543,256 | 9/1985 | Neumeyer | 514/280 |
| 4,569,940 | 2/1986 | Watts | 514/304 |
| 4,624,965 | 11/1986 | Wenig | 514/619 |
| 4,687,773 | 8/1987 | Neumeyer et al. | 514/280 |
| 4,749,686 | 6/1988 | Hintze | 514/12 |
| 4,749,700 | 6/1988 | Wenig | 514/225.2 |
| 4,772,459 | 9/1988 | Sun et al. | 424/10 |
| 4,801,587 | 1/1989 | Voss | 514/248 |
| 4,857,553 | 8/1989 | Ward et al. | 514/557 |
| 5,102,887 | 4/1992 | Goldberg | 514/282 |
| 5,242,391 | 9/1993 | Place et al. | 604/60 |
| 5,270,323 | 12/1993 | Milne Jr. et al. | 514/309 |
| 5,310,561 | 5/1994 | Jao et al. | 424/465 |
| 5,770,606 | 6/1998 | El-Rashidy | 514/284 |

FOREIGN PATENT DOCUMENTS

| | | |
|---|---|---|
| 0 579 435 | 1/1994 | European Pat. Off. . |
| 94 22445 | 10/1994 | WIPO . |

OTHER PUBLICATIONS

Tagliamonte et al., Pharm. Biochem. and Behavior 2;257 (1974).

Laudron et al., Biochem. Pharmacology 28:2161–2165 (1979).

Baldessarini et al., in Gessa et al., eds., vol. 1, *Apomorphine and Other Dopaminomimetics, Basic Pharmacology,* Raven Press, N.Y. (1981), pp. 219–228.

Lal et al., Neural. Transmission 54:75–84 (1982).

Gower et al., European J. Pharmacology 122:239–244 (1986).

Segraves et al., Arch. Sexual Behav. 16(2):125–137 (1987).

Melis et al., Brain Research 415:98–104 (1987).

Lal, Prog. Neuro–Psychopharm. & Biol. Psych. 12:117–164 (1988).

Pehek et al., Pharm. Biochem. and Behavior 31:201–208 (1988).

Danjou et al. Br. J. Clin. Pharmac. 26:733–739 (1988).

Gancher et al., Ann. Neurol. 26:232–238 (1989).

Danjou et al., Pharmacol. Methods 21:61–69 (1989).

Segraves, Arch. Gen. Psych. 46:275–284 (1989).

Panegyres et al., Med. J. Australia 155:371–374 (1991).

Lal et al., J. Psych. Neurosci. 16(5):262–266 (1991).

Heaton et al., J. Urology 145:1099–1102 (1991).

Montastruc et al., Clin. Neuropharmacology 14(5):432–437 (1991).

Durif et al., Eur. J. Clin. Pharmacology 41:493–494 (1991).

Gancher et al., Movement Disorders 6(3):212–216 (1991).

Essink et al., J. Chromatography 570:419–424 (1991).

Segraves et al., J. Urology 145:1174–1175 (1991).

Durif et al., Clinical Neuropharmacology 16(2):157–166 (1993).

Segraves, R.T., Dopamine agonists and their effect on the human penile erectile response, pp. 225–229 in Bancroft, J., editor, *The Pharmacology of Sexual Function and Dysfunction,* Excerpta Medica, Amsterdam (1995).

*Primary Examiner*—Dwayne C. Jones
*Assistant Examiner*—C. Delacroix-Muirheid
*Attorney, Agent, or Firm*—Olson & Hierl, Ltd.

[57] ABSTRACT

Psychogenic impotence can be ameliorated without substantial undesirable side effects by administration of apomorphine and an antiemetic agent in an amount sufficient to substantially reduce nausea symptoms associated with the use of apomorphine.

25 Claims, 13 Drawing Sheets

APOMORPHINE-CONTAINING DOSAGE FORMS FOR AMELIORATING MALE ERECTILE DYSFUNCTION

CROSS-REFERENCE TO RELATED APPLICATIONS

This application is a continuation in part of our application, U.S. Ser. No. 08/546,498 filed on Oct. 20, 1995 and now U.S. Pat. No. 5,770,606, which in turn is a continuation-in-part of U.S. Ser. No. 08/231,250, filed on Apr. 22, 1994, now abandoned.

FIELD OF THE INVENTION

This invention, in one aspect, relates to dosage forms and methods for ameliorating erectile dysfunction in psychogenic male patients. In another aspect this invention relates to diagnosis of erectile dysfunction. More particularly, this invention relates to the use of apomorphine-containing compositions for amelioration of erectile dysfunction in psychogenic male patients and for diagnostic purposes.

BACKGROUND OF THE INVENTION

A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavernosa. Venous outflow is trapped by this enlargement, permitting sustained high blood pressures in the penis sufficient to cause rigidity. Muscles in the perineum also assist in creating and maintaining penile rigidity. Erection may be induced centrally in the nervous system by sexual thoughts or fantasy, and is usually reinforced locally by reflex mechanisms. Erectile mechanics are substantially similar in the female for the clitoris.

Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing.

These descriptions are not exact, however. There is currently no standardized method of diagnosis or treatment. As used herein, psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention).

Various methods for the treatment of impotence have been suggested, including external devices, for example, tourniquets (see U.S. Pat. No. 2,818,855). In addition, penile implants, such as hinged or solid rods and inflatable, spring driven or hydraulic models, have been used for some time. The administration of erection effecting and enhancing drugs is taught in U.S. Pat. No. 4,127,118 to LaTorre. That patent teaches a method of treating male impotence by injecting into the penis an appropriate vasodilator, in particular, an adrenergic blocking agent or a smooth muscle relaxant to effect and enhance an erection. More recently, U.S. Pat. No. 4,801,587 to Voss et al. teaches the application of an ointment to relieve impotence. The ointment consists of the vasodilators papaverine, hydralazine, sodium nitroprusside, phenoxybenzamine, or phentolamine and a carrier to assist absorption of the primary agent through the skin. U.S. Pat. No. 5,256,652 to El-Rashidy teaches the use of an aqueous topical composition of a vasodilator such as papaverine together with hydroxypropyl-$\beta$-cyclodextrin.

Recently the effect of apomorphine on penile tumescence in male patients afflicted with psychogenic impotence has been studied. These studies show that while apomorphine can indeed induce an erection in a psychogenic male patient, the apomorphine dose required to achieve a significant erectile response is usually accompanied by nausea or other serious undesirable side effects such as hypertension, flushing and diaphoresis. The specific mechanisms by which apomorphine acts to produce an erectile response in a human patient are not yet completely understood, however.

Moreover, apomorphine has been shown to have very poor oral bioavailability. See, for example, Baldessarini et al., in Gessa et al., eds., *Apomorphine and Other Dopaminomimetics, Basic Pharmacology*, Vol. 1, Raven Press, N.Y. (1981), pp. 219–228.

Thus the search is continuing for an effective treatment of psychogenic impotence in male patients as well as for diagnostic methods that can identify such patients. It has now been found that certain delivery systems for apomorphine can provide a practical therapeutic and/or diagnostic "window" while reducing the likelihood of undesirable side effects. It has also been found that nausea side effects associated with the use of apomorphine can be substantially reduced by the pre-administration or co-administration of an antiemetic agent.

SUMMARY OF THE INVENTION

It has now been found that, for an optimal erectile response, steady state circulating serum and mid-brain tissue levels of apomorphine are to be maintained within a relatively closely defined range.

Sublingual apomorphine dosage forms, usually containing about 2.5 to about 10 milligrams of apomorphine, have been found to be effective in male patients suffering from psychogenic erectile dysfunction for the induction and maintenance of an erection sufficient for intercourse (i.e., vaginal penetration) without nausea or other undesirable side effects. The apomorphine is administered sublingually, preferably about 15 to about 20 minutes prior to sexual activity, and so as to maintain a predetermined circulating serum levels and mid-brain tissue levels of apomorphine during the period of sexual activity sufficient to induce an erection adequate for vaginal penetration but less than the amount that induces nausea. The plasma concentration of apomorphine should be maintained at no more than about 5.5 nanograms per milliliter, preferably about 0.3 to about 4 nanograms per milliliter, and more preferably about 1 to about 2 nanograms per milliliter.

The foregoing sublingual apomorphine dosage forms are also suitable for screening patients complaining of erectile dysfunction so as to identify patients of psychogenic etiology.

The nausea side effect associated with the use of apomorphine can be substantially reduced by administration of an antiemetic agent. Specifically, a method suitable for treating erectile dysfunction in a male patient comprises administering to the patient prior to sexual activity, an antiemetic agent in an amount sufficient to substantially reduce nausea associated with use of apomorphine, and apomorphine in an amount sufficient to induce and maintain an erection adequate for vaginal penetration.

The antiemetic agent is preferably co-administered with the apomorphine in a single sublingual dosage unit. Separate dosage units with differing delivery routes are also suitable for practicing the present invention, however. For example, the antiemetic agent and apomorphine may be administered to the patient sequentially by first administering a composition comprising an antiemetic agent and thereafter a composition comprising apomorphine.

A dosage unit for administering the antiemetic-apomorphine combination comprises an antiemetic agent as a relatively faster release component and apomorphine as a component released after release of the antiemetic agent has begun. This staggered release dosage unit is preferably a layered tablet having a core portion containing the apomorphine and an outer layer portion containing the antiemetic agent.

A sublingual tablet for administering the antiemetic-apomorphine combination comprises apomorphine, an antiemetic agent, an osmotic agent and a swellable hydrophilic carrier. The preferred osmotic agent is mannitol, while the preferred swellable hydrophilic carrier is microcrystalline cellulose.

The practice of this invention using apomorphine and an antiemetic agent also can be applied to the treatment of severe motor fluctuations in Parkinson's disease.

DETAILED DESCRIPTION OF THE PREFERRED EMBODIMENTS

Figure 1:
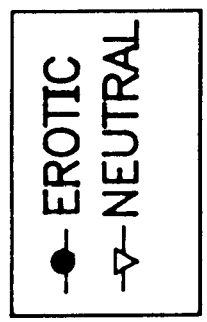
FIG. 1 is a graphical representation of mean erectile function, expressed as RIGISCAN™ monitor value, as a function of apomorphine dose.
Figure 1:
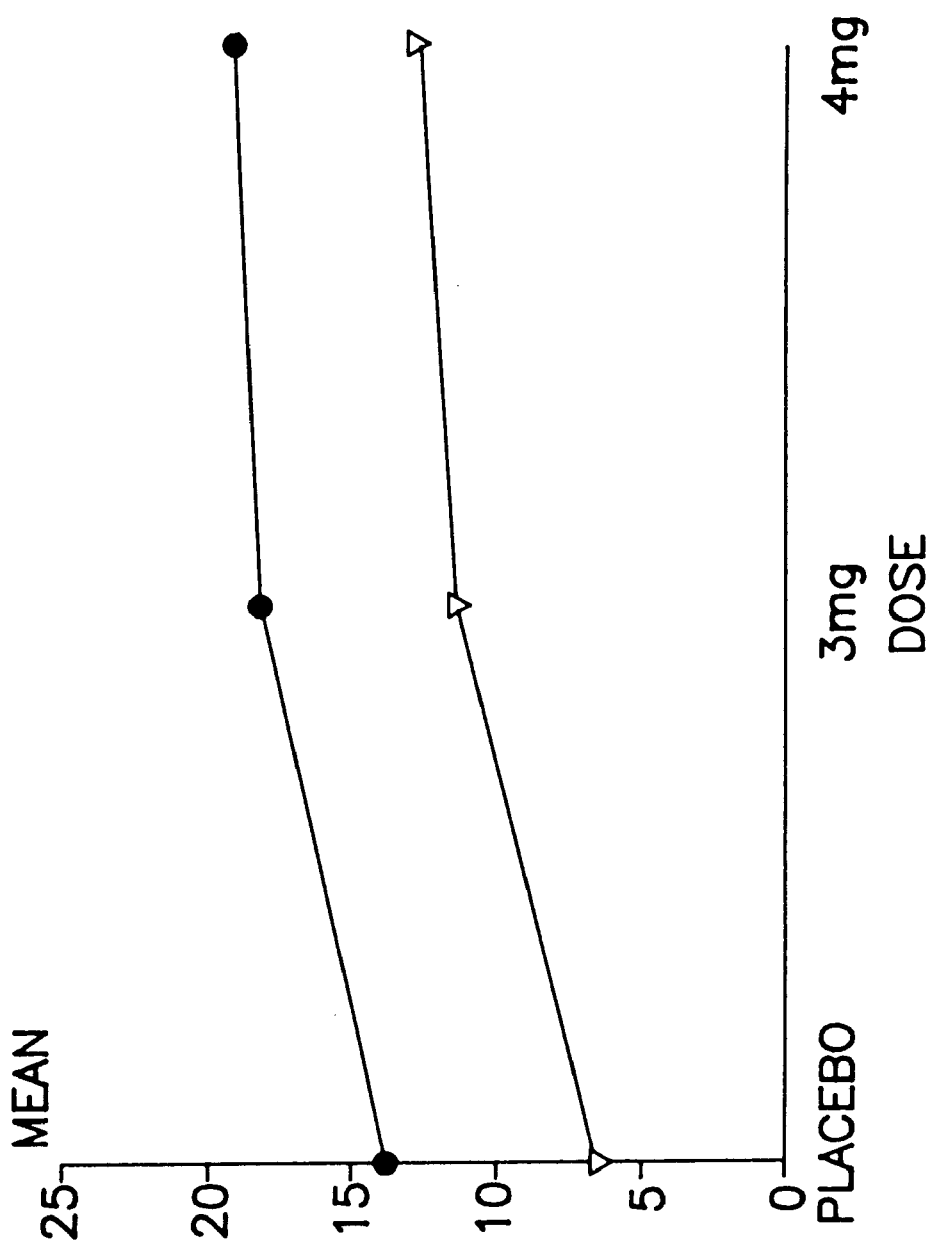

Apomorphine is a dopamine receptor agonist that has a recognized use as an emetic when administered subcutaneously in about a 5-milligram dose. For the purposes of the present invention, apomorphine or a similarly acting dopamine receptor agonist is administered in an amount sufficient to excite cells in the mid-brain region of the patient but with minimal side effects. This cell excitation is believed to be part of a cascade of stimulation that is likely to include neurotransmission with serotonin and oxytocin.

The dopamine receptors in the mid-brain region of a patient can be stimulated to a degree sufficient to cause an erection by the sublingual administration of apomorphine so as to maintain a plasma concentration of apomorphine of no more than about 5.5 nanograms per milliliter (5.5 ng/ml). The sublingual administration usually takes place over a time period in the range of about 2 to about 10 minutes, or longer. The amount of apomorphine administered sublingually over this time period preferably is in the range of about 25 micrograms per kilogram ($\mu$g/kg) of body weight to about 60 $\mu$g/kg of body weight.

The apomorphine is administered preferably about 15 to about 20 minutes prior to sexual activity.

Apomorphine can be represented by the formula

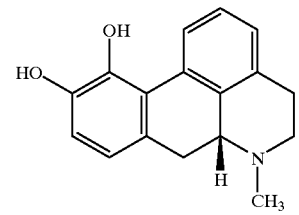

and exists in a free base form or as an acid addition salt. For the purposes of the present invention apomorphine hydrochloride is preferred; however, other pharmacologically acceptable moieties thereof can be utilized as well. The term "apomorphine" as used herein includes the free base form of this compound as well as the pharmacologically acceptable acid addition salts thereof. In addition to the hydrochloride salt, other acceptable acid addition salts are the hydrobromide, the hydroiodide, the bisulfate, the phosphate, the acid phosphate, the lactate, the citrate, the tartarate, the salicylate, the succinate, the maleate, the gluconate, and the like.

Illustrative preferred sublingual dosage forms are set forth in Table I, below.

TABLE I

150-Milligram Apomorphine Hydrochloride Sublingual Tablets

| 3-mg Tablet | |
|---|---|
| Apomorphine Hydrochloride | 2.00 wt % |
| Mannitol | 66.67 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium Stearate | 0.33 wt % |
| 4-mg Tablet | |
| Apomorphine Hydrochloride | 2.66 wt % |
| Mannitol | 66.00 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium Stearate | 0.33 wt % |
| 5-mg Tablet | |
| Apomorphine Hydrochloride | 3.33 wt % |
| Mannitol | 65.34 wt % |
| Ascorbic Acid | 3.33 wt % |
| Citric Acid | 2.00 wt % |
| Avicel PH102 | 15.00 wt % |
| Methocel E4M | 10.00 wt % |
| Aspartame | 0.67 wt % |
| Magnesium Stearate | 0.33 wt % |

If desired, and in order to facilitate absorption and thus bioavailability, the presently contemplated dosage forms can also contain, in addition to tabletting excipients, β-cyclodextrin or a β-cyclodextrin derivative such as hydroxypropyl-β-cyclodextrin (HPBCD). Illustrative dosage forms containing HPBCD are shown in Tables II and III, below.

TABLE II

Apomorphine Hydrochloride Sublingual Tablets With Hydroxypropyl-β-Cyclodextrin

| | mg/Tab |
|---|---|
| Apomorphine Hydrochloride | 4.0 |
| HPBCD | 5.0 |
| Ascorbic Acid | 10.0 |
| PEG8000 | 39.5 |
| Mannitol | 39.5 |
| Aspartame | 2.0 |
| TOTAL | 100.0 |

TABLE III

Apomorphine Hydrochloride Sublingual Tablets With β-Cyclodextrin

| | mg/Tab |
|---|---|
| Apomorphine Hydrochloride | 5.0 |
| β-Cyclodextrin | 20.0 |
| Ascorbic Acid | 5.0 |
| Mannitol | 68.9 |
| Magnesium Stearate | 1.0 |
| D&C Yellow 10 Aluminum Lake | 0.1 |
| TOTAL | 100.0 |

The onset of nausea can be obviated or delayed by delivering apomorphine at a controlled dissolution rate so as to provide circulating serum levels and mid-brain tissue levels of apomorphine sufficient for an erection without inducing nausea. When apomorphine is administered at or near the relatively higher amounts of the aforementioned dosage range, the likelihood of nausea onset can be reduced by concurrent administration of a ganglionic agent (inhibitor of ganglionic response) such as nicotine or lobeline sulfate. For this purpose, the weight ratio of apomorphine to ganglionic agent is in the range of about 300:1 to about 5:1.

The preferred weight ratio necessarily varies according to the potency of the agent employed, however. When nicotine is used, the preferred weight ratio of apomorphine to nicotine is in the range of about 10 to about 1. With regard to specific drug loadings, sublingual dosage units for co-administration of nicotine and apomorphine preferably contain apomorphine in the range of about 1 to about 8 milligrams (mg) and nicotine in the range of about 0.25 to about 3 mg. A particularly preferred sublingual combination dosage unit contains apomorphine in the range of about 4 mg to about 8 mg, and nicotine in the range from about 0.75 mg to about 1.25 mg.

Nicotine and lobeline sulfate have been classified as ganglionic stimulating alkaloids. See, for example, Goodman, Louis S. and Alfred Gilman, eds., *The Pharmacological Basis of Therapeutics,* 5th Ed., MacMillan Publishing Co., New York, N.Y. (1975), pp. 567–569. For the purposes of the present invention, ganglionic stimulating alkaloids such as nicotine and lobeline sulfate serve as antiemetic agents.

Antiemetic agents are drugs that prevent or substantially reduce nausea and vomiting. As used herein, the terms "antiemetic agent" and "antinausea agent" are interchangeable and mean a pharmaceutically acceptable compound that substantially reduces nausea symptoms. As described below, antiemetics may be classified according to their structure or their mechanism of operation.

In addition to the ganglionic stimulating alkaloids discussed above, other antiemetic agents that can be used in conjunction with apomorphine are antidopaminergic agents such as metoclopramide, and the phenothiazines, e.g., chlorpromazine, prochlorperazine, pipamazine, thiethylperazine, oxypendyl hydrochloride, promazine, triflupromazine, propiomazine, acepromazine, acetophenazine, butaperazine, carphenazine, fluphenazine, perphenazine, thiopropazate, trifluoperazine, mesoridazine, piperacetazine, thioridazine, pipotiazine, pipotiazine palmitate, chlorprothixine, thiothixine, doxepin, loxapin, triflupromazine, methdilazine, trimeprazine, methotrimeprazine, and the like. Metoclopramide is a benzamide. Benzamides are a recognized group of antiemetics that are suitable for the present invention and include in addition to metoclopramide, trimethobenzamide and benzquinamid, as well as others. Also suitable are the serotonin (5-hydroxytryptamine or 5-HT) antagonists such as domperidone, odansetron (commercially available as the hydrochloride salt under the designation Zofran®), and the like, the histamine antagonists such as buclizine hydrochloride, cyclizine hydrochloride, dimenhydrinate (Dramamine), and the like, the parasympathetic depressants such as scopolamine, and the like, as well as other antiemetics such as metopimazine, trimethobenzamide, benzquinamine hydrochloride, diphenidol hydrochloride, and the like.

Another suitable group of antiemetics are the meclizines which include, for example, meclizine, chlorcyclizine, cyclizine, and buclizine.

Accordingly, a composition aspect of the present invention provides a combination of apomorphine and an antiemetic agent which is a member of the group consisting of the phenothiazines, the benzamides, the meclizines, the serotonin antagonists, hydroxyzine, lobeline sulfate, dimenhydrinate, scopolamine, metopimazine, diphenidol hydrochloride, nicotine, and their acid addition salts.

Any pharmaceutically acceptable form of the antiemetic agents can be employed, i.e., the free base or a pharmaceutically acceptable salt thereof (e.g. cyclizine hydrochloride, cyclizine acetate, diphenhydramine hydrochloride, meclizine hydrochloride, etc.)

The nausea side effect associated with the use of apomorphine can be substantially reduced by administration of an antiemetic agent. Specifically, a method suitable for treating erectile dysfunction in a male patient comprises administering to the patient (prior to sexual activity) an antiemetic agent in an amount sufficient to substantially reduce nausea associated with use of apomorphine, and apomorphine in an amount sufficient to induce and maintain an erection adequate for vaginal penetration.

For treatments according to the present invention, an antiemetic agent may be co-administered with apomorphine or may be administered concurrently or sequentially with apomorphine to substantially reduce the symptoms of nausea associated with the use of apomorphine. By the term "co-administration" is meant the administration of both apomorphine and an antiemetic agent to the patient in a single unit dosage form as, for example, in a layered tablet. "Concurrent" administration denotes the substantially simultaneous administration of the two drugs in separate unit dosage forms, while "sequential" administration is the administration of separate dosage forms of the two drugs with one being administered at some time interval after the other. The co-administration of an antiemetic agent and apomorphine is preferred and allows for a higher dose of apomorphine with generally improved response and function.

When the antiemetic agent prochlorperazine hydrochloride is used, the preferred weight ratio of apomorphine hydrochloride to prochlorperazine hydrochloride is in the range of about 5 to about 0.25. The amount of prochlorperazine hydrochloride administered sublingually preferably is in the range of about 5 $\mu$g/kg of body weight to about 200 $\mu$g/kg of body weight.

Apomorphine with antiemetic-containing dosage forms including nicotine-containing dosage forms and domperidone-containing dosage forms are illustrated in Table IV, below.

TABLE IV

Apomorphine Hydrochloride Sublingual Tablets Containing an Antiemetic Agent

|  | mg/Tab |
| --- | --- |
| Apomorphine Hydrochloride | 5.0 |
| Ascorbic Acid | 5.0 |
| Mannitol | 67.9 |
| Magnesium Stearate | 1.0 |
| Nicotine | 1.0 |
| β-Cyclodextrin | 20.0 |
| D&C Yellow 10 Aluminum Lake | 0.1 |
| TOTAL | 100.0 |
| Apomorphine Hydrochloride | 5.0 |
| Ascorbic Acid | 5.0 |
| Mannitol | 58.9 |
| Magnesium Stearate | 1.0 |
| Domperidone | 10.0 |
| β-Cyclodextrin | 20.0 |

TABLE IV-continued

Apomorphine Hydrochloride Sublingual Tablets Containing an Antiemetic Agent

|  | mg/Tab |
| --- | --- |
| D&C Yellow 10 Aluminum Lake | 0.1 |
| TOTAL | 100.0 |
| Apomorphine Hydrochloride | 4.0 |
| Nicotine Base | 1.0 |
| Acesulfame-K | 4.0 |
| Microcrystalline Cellulose | 37.5 |
| Peppermint Flavor | 2.5 |
| Chocolate Flavor | 2.0 |
| Citric Acid | 3.0 |
| Hydroxypropylmethylcellulose | 13.0 |
| Mannitol | 80.0 |
| Magnesium Stearate | 3.0 |
| TOTAL | 150.0 |
| Tablet core: | |
| Apomorphine Hydrochloride | 4.0 |
| Acesulfame-K | 1.6 |
| Microcrystalline Cellulose | 21.6 |
| Peppermint Flavor | 1.0 |
| Chocolate Flavor | 0.8 |
| Citric Acid | 1.2 |
| Hydroxypropylmethylcellulose | 4.0 |
| Mannitol | 24.6 |
| Magnesium Stearate | 1.2 |
| Tablet outer layer: | |
| Nicotine Base | 1.0 |
| Acesulfame-K | 0.4 |
| Microcrystalline Cellulose | 36.6 |
| Mannitol | 47.0 |
| Hydroxypropylmethylcellulose | 4.0 |
| Magnesium Stearate | 1.0 |
| TOTAL | 150 |
| Apomorphine Hydrochloride | 4.0 |
| Prochlorperazine Hydrochloride | 5.0 |
| Acesulfame-K | 4.0 |
| Microcrystalline Cellulose | 37.5 |
| Peppermint Flavor | 2.5 |
| Chocolate Flavor | 2.0 |
| Citric Acid | 3.0 |
| Hydroxypropylmethylcellulose | 10.0 |
| Mannitol | 68.0 |
| Sodium Alginate | 10.0 |
| Magnesium Stearate | 3.0 |
| TOTAL | 150.0 |
| Tablet core: | |
| Apomorphine Hydrochloride | 4.0 |
| Acesulfame-K | 1.6 |
| Microcrystalline Cellulose | 20.0 |
| Peppermint Flavor | 1.0 |
| Chocolate Flavor | 0.8 |
| Citric Acid | 1.2 |
| Hydroxypropylmethylcellulose | 5.0 |
| Mannitol | 20.2 |
| Sodium Alginate | 5.0 |
| Magnesium Stearate | 1.2 |
| Tablet outer layer: | |
| Prochlorperazine | 5.0 |
| Acesulfame-K | 0.4 |
| Microcrystalline Cellulose | 35.6 |
| Mannitol | 46.0 |
| Hydroxypropylmethylcellulose | 2.0 |
| Magnesium Stearate | 1.0 |
| TOTAL | 100.0 |

For improved bioavailability, controlled release, and reliable dosage control, the apomorphine containing compositions of the present invention are preferably administered sublingually. The preferred sublingual dosage forms dissolve within a time period of at least about 2 minutes but less than about 10 minutes. The dissolution time can be longer, however, if desired as long as the necessary plasma concentration of apomorphine can be maintained. More preferably, the dissolution time in water for the presently contemplated dosage forms is about 3 minutes to about 5 minutes.

The methods and compositions of the present invention are not limited to sublingual drug delivery, however. Antiemetic agents of the present invention may be delivered to patients using other conventional drug delivery methods, such as orally, intravenous injection, subcutaneous injection, suppository, or patch (e.g. buccal patch). In addition, patients may receive the antiemetic agent and the apomorphine via different delivery mechanisms. For example, the apomorphine may be delivered via sublingual tablet, while the antiemetic agent is delivered orally.

When an antiemetic agent is used, the antiemetic agent is preferably made available before the apomorphine. This can be accomplished not only by administering the antiemetic agent before the apomorphine but also by employing a staggered release dosage form as described below. The present invention is also not limited to a particular sequence of administration or dosage form for the antiemetic agent and apomorphine. If desired, the antiemetic agent may be administered substantially concurrently (i.e., at the same time as) or even after the apomorphine. For example, a separate dosage form of an antiemetic agent can be made available to patients for use after administration of the apomorphine if nausea symptoms are encountered.

The antiemetic agent preferably is delivered to the patient with the apomorphine via a single dosage unit. Provided for this purpose, a sublingual tablet comprises apomorphine, an antiemetic agent, an osmotic agent, and a swellable hydrophilic carrier. A preferred swellable hydrophilic carrier is microcrystalline cellulose. Other suitable swellable hydrophilic carriers for the present purposes are ethyl cellulose, microcrystalline cellulose, cross-linked polyvinyl pyrrolidone, dicalcium phosphate, calcium carbonate and silica.

Suitable osmotic agents include monosaccharide and disaccharide sugars, such as glucose, fructose, mannitol, sorbitol, lactose, and sucrose. Glycerin or urea may also be used. Organic and inorganic salts, such as sodium chloride, potassium chloride and water soluble polyelectrolytes, are also suitable as osmotic agents. A preferred osmotic agent is mannitol. Preferred embodiments of a sublingual tablet according to the present invention also contain a lubricant such as magnesium stearate.

The present invention provides an apomorphine/antiemetic combination formulated into a dosage unit that provides a staggered release of antiemetic agent and apomorphine. Specifically, a dosage unit includes an antiemetic agent as a relatively faster release component and apomorphine as a component released after release of the antiemetic agent has begun. Defined in terms of release rate, one preferred apomorphine/antiemetic dosage unit obtains 50 percent release of the antiemetic agent at least 5 minutes before obtaining 50 percent release of the apomorphine.

For this staggered release purpose, the present invention further provides a layered tablet that comprises a core layer containing apomorphine and an outer layer containing an antiemetic agent. Table IV (above) as well as the Examples below contain illustrative compositions for layered tablets.

Illustrative preferred sublingual dosage forms for apomorphine/antiemetic combinations are set forth in the Examples 1–7.

The present invention is illustrated further by the following studies which were focused on two specific objectives. The first was to determine whether, relative to placebo response, patients who presented with "psychogenic" impotence (i.e., patients who were still capable of achieving erections) demonstrated improved erectile function and/or enhanced sexual desire post-dosing with sublingual apomorphine (APO). The second objective was to determine what dose(s) of various forms of sublingual APO are effective in this group of patients for inducing an erection that is sufficient for vaginal penetration.

Participating patients were selected from among those that initially presented with the complaint of impotence. These patients underwent a thorough urological assessment by a urologist as well as an assessment by a psychiatrist. Diagnostic testing for erectile difficulties was extensive and included the following: biochemical profile, nocturnal penile tumescence (NPT) monitoring, doppler flow studies, biothesiometry, corporal calibration testing with an intracorporal injection of triple therapy and dynamic cavernosometry. These tests were used to rule out any arterial, venous or peripheral neural causality of impotence. Any patients with abnormalities in any of these three areas were excluded from entry to the trials. The inclusion/exclusion criteria for all four pilot studies are set forth in Table V, below. Patients who met all criteria were diagnosed as having impotence primarily of a psychogenic origin. If there were no known medical contraindications to the use of a dopaminergic medication they were offered entry into an APO trial.

Instructions were given regarding the protocol by the research clinician, and an informed consent was obtained. Patients were advised that they were free to withdraw from the trial at any time without penalty or prejudice. They were tested on at least three separate days at three separate doses (placebo and two active medication doses) with an interval of no less than three days between. The experimental scheme described below was used in all four pilot studies.

Patients were seated in a comfortable chair and a RIGISCAN™ ambulatory tumescence monitor (Dacomed Corp., Minneapolis, Minn.) was placed on the patient and the computer was set in the real time monitoring mode. Blood pressure and heart rate were recorded pre-dosing with APO or placebo and at the end of the testing session. Visual analogue scales (VAS) were completed by the patient pre-dosing as well as post-dosing (at the end of the testing session). These scales reflected the patient's sense of well being, level of sedation, tranquilization, anxiousness, arousal and any changes in yawning behavior. In a single-blind fashion, apomorphine or placebo was administered to the patient sublingually. Doses of active medication varied on the formulation of the apomorphine administered (liquid or tablet). Because of the possibility of nausea and the tolerance to this effect that prior dosing conveys, the patient was given increasing doses at each testing. However, the patient was unaware of the dose that he was receiving (single-blind). Patients were instructed not to swallow the medication, but to keep it under their tongue and allow it to be absorbed there.

Symptoms as they were volunteered were recorded by the research clinician. If the patient complained of nausea or felt unwell in any way he was asked if he wanted to abort the trial. If the trial was aborted, the patient was given Gravol 50 mg p.o. at that time. The patient was monitored by the research clinician until these side-effects had subsided. He was asked to return the following week for retesting at the same dose and was instructed to begin treatment with Domperidone 10 m.g. p.o. TID the day before and morning of his next session.

Patients not experiencing nausea or any other significant adverse effects within fifteen minutes post-dosing with APO or placebo viewed segments of standardized erotic videos to provide sexual stimulation. The following sequence of videos was viewed: a ten minute erotic video, a neutral video lasting between five and ten minutes in duration and finally another ten minute erotic video. The duration of the testing session for each dose level lasted between 45 and 60 minutes. After determining the most effective dose of apomorphine for the patient, he was then offered APO for domestic trial at that dose.

Results of Pilot Studies 1 to 4

The frequency and the magnitude of erectile responses were documented with each dose of apomorphine or placebo. Data obtained from the RIGISCAN™ monitor was downloaded and each session was scanned. Erection responses were then scored for rigidity (%) and tumescence (cm.) at both the tip and base of the penis and an overall score was given that corresponded to these parameters during the viewing of both erotic and neutral video segments (see Table VI, below). A score of less than 16 indicated erectile dysfunction and a poor response to apomorphine at that dose.

Visual analogue scales (See Table IX) were compared both pre- and post-dosing, and examined for changes in feeling of well being, levels of arousal, anxiousness, sedation/tranquilization and yawning behavior. Blood pressure and heart rate were also compared pre- and post-dosing.

Effects of apomorphine that were both reported to and observed by the research clinician were grouped into two categories: Adverse Effects (i.e., flushing, diaphoresis, nausea, vomiting, changes in blood pressure or heart rate) or Primary Effects (i.e., yawning and erections).

Each pilot study was reviewed under the categories mentioned above.

Pilot Study #1

The initial formulation evaluated was liquid apomorphine administered via sublingual route. APO was prepared by a clinic pharmacist and dissolved in a solution of sodium metabisulfite and ethylenediamine tetraacetic acid (EDTA). The final concentration was 100 mg/ml. Patients were tested on three separate occasions at three separate doses (placebo; 10 mg; 20 mg).

Twelve patients entered into this trial. All patients had reported erectile dysfunction greater than 1 year in duration. The age range in this group was from 38 to 60 years. One patient withdrew after placebo and another withdrew after adverse effects at the 20 mg dose. That left a total evaluable group of ten. All ten patients had previously received yohimbine HCl for erectile dysfunction. Eight had failed a trial of yohimbine HCl. Of this group of eight, 6 were successful with apomorphine.

Seven (70%) were successes (score of no less than 16 on both neutral and erotic video segments; Table VI) and three (30%) were categorized as failures with apomorphine. Six out of the seven successful patients continued on with a domestic trial of apomorphine at the dose that gave them the best response during testing. Three required treatment with Domperidone the day before and morning of apomorphine usage. The range of domestic use varied from two to seven months.

Analysis of visual analogue scales pre- and post-dosing with apomorphine indicated the following. At the end of the session patients were relaxed but not sedated. There was no evidence of arousal or anxiousness. Yawning behavior changes were evident on these scales with the incidence of yawning increasing between 15 and fifty minutes post-dosing and with each increase in dosing. Each patient experienced between two to five yawns per session. These changes were not evident with placebo.

The primary effect of yawning was both reported by patients and observed at both 10 mg and 20 mg doses. No yawning was reported with placebo. Adverse effects were reported at both dose levels. Two patients who did not experience nausea or diaphoresis were researched for similarities in their patient profiles but none were found. Anywhere from ten to fifteen minutes post-dosing the other eight patients developed sudden onset of various levels of nausea (and in one instance vomiting), diaphoresis, dizziness, double or blurred vision, decrease in both blood pressure and heart rate and pale or ashen coloring. Side effects varied from being transient and brief to lasting as long as from 30 to 40 minutes. One patient reported a stuffy nose starting approximately 30 minutes post-dosing and lasting for approximately 10 minutes. No adverse effects were reported post placebo dosing.

The foregoing Pilot Study leads to the following conclusions:

1. Apomorphine is effective in inducing erectile episodes without increasing libido in the "psychogenically" impotent male.

2. Both 10 mg and 20 mg doses produce erectile responses.

3. Both doses produced adverse effects (nausea, vomiting, diaphoresis, etc.) that would be unacceptable to patients and their partners, however. These effects can be counteracted with the use of Domperidone.

Pilot Study #2

The first sublingual tablet formulations evaluated were 2.5 and 5 mg. Patients were tested on three separate occasions at three separate doses (placebo; 2.5 mg, 5 mg).

A total of eight patients entered into this trial. All patients reported erectile difficulties for more that two years. The age range was from 38 to 62 years. All had failed a trial of yohimbine HCl. One patient withdrew from the trial after experiencing adverse effects at the 5 mg dose. That left a total of seven evaluable patients.

Two (29%) were successes (score of no less than 16; Table VI) and five (71%) were failures during lab testing. The two successful patients went onto a domestic trial of apomorphine at the 2.5 mg dose which was the most effective and did not produce adverse effects. Both patients used apomorphine at home for no less than two months with satisfactory results.

Analysis of visual analogue scales pre- and post-dosing with apomorphine indicated the same trends as with the liquid apomorphine preparation. Patients were relaxed but not sedated. No evidence of arousal or anxiousness was noted.

The primary effect of yawning was both reported by patients and observed at both 2.5 mg and 5 mg doses. The incidence of yawning increased between fifteen and forty minutes post-dosing. At the 2.5 mg dose all patients who failed testing had only one or two yawns per session. The 5 mg dose not only produced adverse effects (nausea, diaphoresis, dizziness, blurred vision, facial flushing, drop in both heart rate and blood pressure) but also increased yawning responses to three to five times per session. The two successful patients experienced three to five yawns at both the 2.5 mg and 5 mg doses. These changes were not evident with placebo.

At the end of Pilot Study #2 the following conclusions were made:

1. There appears to be a correlation between the effectiveness of the dose and yawning response (poor responders experience less yawning).

2. Both 2.5 and 5 mg doses produced erectile responses in some patients. The apparent 28% success rate was because of lab use only (failures were not given drug to take home) and lack of available intermediate doses.

3. In some instances the 5 mg dose can produce adverse effects (i.e., nausea, diaphoresis, etc.) that may be unacceptable to patients and their partners. These effects can be counteracted with the administration of Domperidone or nicotine (e.g., by smoking).

4. The sublingual tablets were easy to administer and dissolved within five minutes.

Pilot Study #3

Apomorphine was evaluated as an aqueous intranasal spray (1.25 mg per puff). The first patient was an anxious, 53 year old male who had been experiencing erectile dysfunction for two years. This patient had previously failed a trial of yohimbine.

He was tested on three separate occasions at three separate doses (placebo, 2.5 mg; 3.75 mg) and was categorized as a failure with the score of less than sixteen on both erotic and neutral video segments. He experienced yawning with both 2.5 mg and the 3.75 mg and was successful with this trial for two months until he inadvertently increase the dose. Adverse effects occurred within five minutes post-dosing (nausea and vomiting, dizziness, double and blurred vision, diaphoresis, and ashen coloring). The patient refused to retry medication after this incident. He stated he did not like this formulation.

Patient No. 2 was twenty-one year old male with erectile problems of a duration of three years. He had failed a previous course of yohimbine HCl. Ten minutes post-dosing with apomorphine at 2.5 mg he experienced yawing for a total of five yawns, and then experienced immediately major hemodynamic adverse effects. These included pale and ashen coloring, diaphoresis, nausea and vomiting, blurred vision, hypotension with a blood pressure of 70/50. Twenty minutes post adverse effect, vital signs were stable. The patient was feeling well, and coloring was good. This patient was then dropped from further testing.

Although the intranasal administration was effective in eliciting an erection, further testing of this intranasal formulation of apomorphine was discontinued because of possible overdose and increased side effects. The foregoing experience illustrates the need for reliable and relatively safer dosage forms.

Pilot Study #4

New sublingual tablet formulations of apomorphine at 3, 4 and 5 mg doses (Table I, above) were evaluated. Patients were tested on at least three separate occasions on at least three separate doses (placebo; 3 mg; and 4 mg). A 5 mg sublingual dose was also tested in some patients. The results of this study are summarized in Tables VII and VIII A–C, below.

To date, twelve patients have been completely evaluated on this formulation. All patients reported erectile dysfunction for more than two years. The patients' age range was thirty-nine to sixty-six years. Three patients had been successful with yohimbine HCl in the past, and two had previously not tried this compound. Seven patients of this group of twelve had previously failed a trial of yohimbine HCl. Of this latter group of seven, four were successfully treated with apomorphine.

Eight (67%) have been successful with apomorphine to date. Four (33%) were failures with apomorphine. Both 3 mg and 4 mg doses produced erectile responses. Several patients went on to a trial of the 5 mg sublingual dose which did not appear to be more effective than the relatively lesser doses in terms of erectile response. All eight of the successful patients continued on with the domestic use for a time period of one to four months. All patients reported good erectile activity and no side effects.

Analysis of visual analogue scales, both pre- and post-dosing with apomorphine, again indicated that the patients were relaxed but not sedated, and did not have feelings of arousal or anxiousness post-dosing. The new formulations tested (3 mg; 4 mg; and 5 mg) were devoid of adverse effects. The patients felt well post testing, and did not report or demonstrate any adverse effects that had traditionally been seen with the administration of precious apomorphine liquid and intranasal preparations (Pilot Studies No. 1 and No. 3). The primary effect of yawning was still reported and observed at all doses, but the number and frequency of yawns was small (one or two).

The foregoing pilot study shows that 3-mg, 4-mg and 5-mg apomorphine doses are effective in inducing penile erections, and also that there are no serious adverse effects with these preparations. Domestic use of these preparations was well accepted by patients and their partners. They were content with the convenience of dosing approximately fifteen minutes prior to sexual activity. All patients have stated that this was more acceptable than dealing with dosing on a routine basis.

TABLE V

Inclusion/Exclusion Criteria

INCLUSION CRITERIA:

1. Age 18–66 years.
2. NPT circumference increase of 1.5 cm or more on one night and >70% rigidity.
3. ICI circumference increase of 1.5 cm or more and >70% rigidity.

EXCLUSION CRITERIA:

1. Currently severe or life threatening systemic disease.
2. Clinically significant ECG abnormalities.
3. Personal or first degree family history of epilepsy.
4. Abnormal: Hepatic/renal function
   Hematology
5. Low: pre-trial testosterone
   Low or High: LH
   High: Prolactin
6. Hypertension requiring treatment.
7. History of depression requiring treatment with antidepressants, ECT, or hospitalization.
8. Symptomatic ischemic heart disease/or MI within the last three months.
9. Diabetes.
10. Failure to obtain informed consent.
11. Legal cases.
12. Unable or unwilling to comply with protocol.
13. Drinks more than (on average) 45 units alcohol per week/or uses illicit drugs.
14. History of syncope.
15. Prohibited Drugs: sympathetic or parasympathetic types drugs, Beta blockers, Vasodilators, psychotropic medications, tranquilizers, thiazides, Captopril, Verapmil, Furosemide, Spironolactone, Metoclopramide, Cimetidine or other drugs which are likely to influence erectile function.

TABLE VI

Response to Erotic Videotape

|  | Score |
|---|---|
| 1. Maximum increase in penile circumference Circumference (cms.) | |
| 0–<0.5 cm. | 0 |
| 0.5–<1.0 cm. | 1 |
| 1.0–<1.5 cm. | 2 |
| 1.5–<2.0 cm. | 3 |
| 2.0–<2.5 cm. lasts <1 min. | 4 |

TABLE VI-continued

Response to Erotic Videotape

| | Score |
|---|---|
| 2.5 or more lasts <1 min. | 5 |
| 2.0–<2.5 cm. lasts at least 1 min. | 6 |
| 2.5 or more lasts at least 1 min. | 7 |
| 3.0 or more lasts at least 5 min. | 8 |
| 3.0 or more lasts at least 10 min. | 9 |
| A. Maximum increase in penile tip circumference | ____ |
| B. Maximum increase in penile basal circumference | ____ |
| 2. Maximum penile rigidity | |
| Rigidity (%) | |
| 0–<10 | 0 |
| 10–<20 | 1 |
| 20–<30 | 2 |
| 30–<40 | 3 |
| 40–<50 | 4 |
| 50–<60 | 5 |
| 60–<70 | 6 |
| 70–<80 | 7 |
| 80–<90 | 8 |
| 90–100 | 9 |
| C. Maximum penile tip rigidity | ____ |
| D. Maximum penile basal rigidity | ____ |
| 3. Total score (A, B, C & D)  ____ | ____ |
| A score of less than 16 indicates erectile dysfunction | |

Akaike's criterion. Table VIII B presents the statistical results for the main effects of treatment and of stimulus, for the treatment by stimulus interaction, and for orthogonal contrasts within the erotic and neutral conditions. It can be seen that the treatment main effect (i.e., general difference across treatment conditions without regard to stimulus background) is statistically significant; that the main effect of stimulus (i.e., general difference across stimulus backgrounds without regard to treatment) is statistically significant; and that the treatment by stimulus interaction is not statistically significant. These findings imply that active treatment is more effective than placebo and that this finding, although stronger when using an erotic stimulus, is true regardless of stimulus background (see FIG. 1). The orthogonal (statistically independent) contrasts confirm that active treatment is superior at a statistically significant level under both erotic and neutral conditions, but also indicate that the difference between the 3 mg and 4 mg dose does not exceed that expected by chance for the number of patients (12) used in this study.

B. Percent Successful Erectile Function

Figure 2:
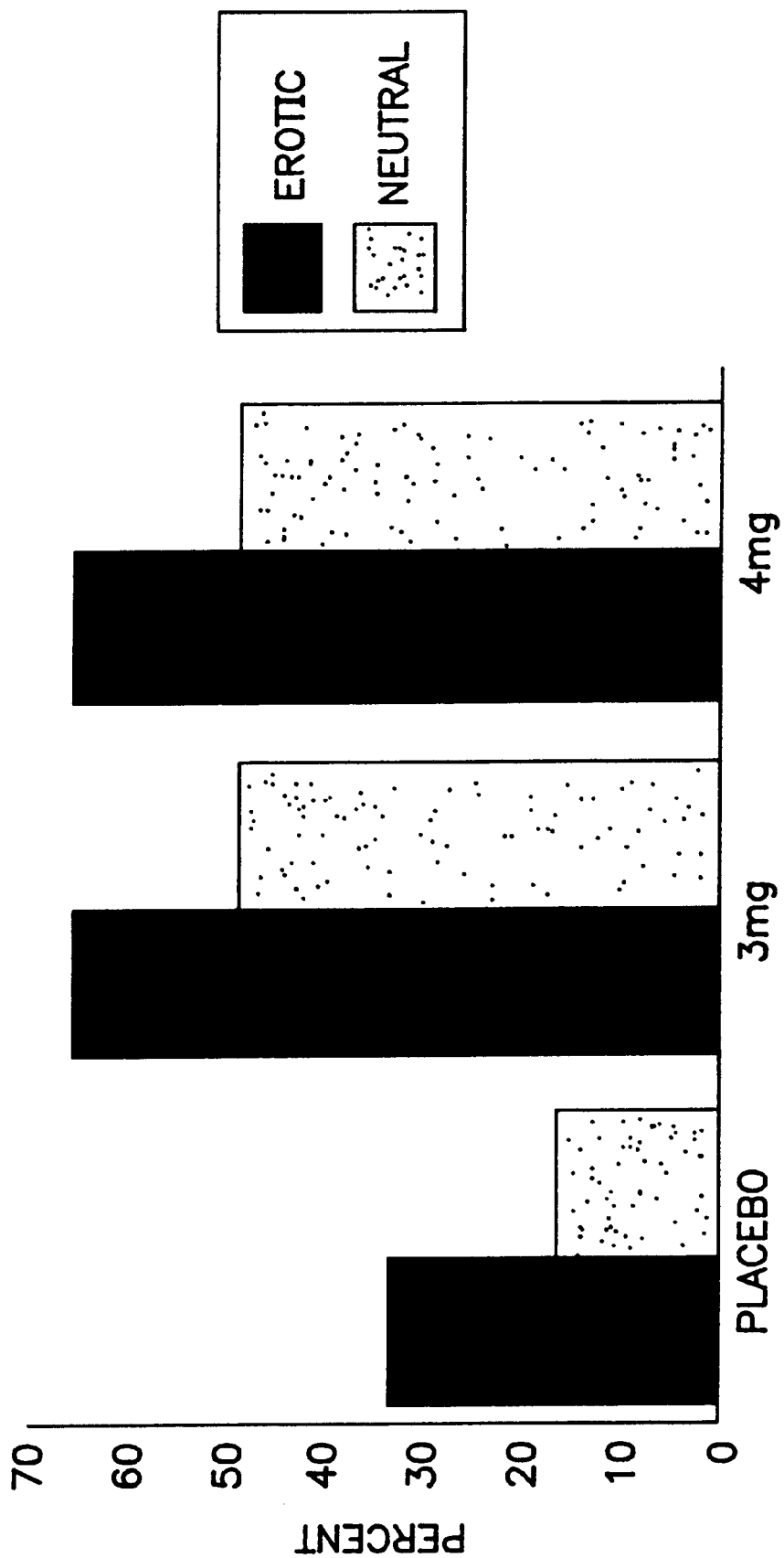
FIG. 2 is a bar graph depicting the percent successful erectile function for placebo, 3-milligram apomorphine dose, and 4-milligram apomorphine dose under erotic and neutral conditions.
Figure 3:
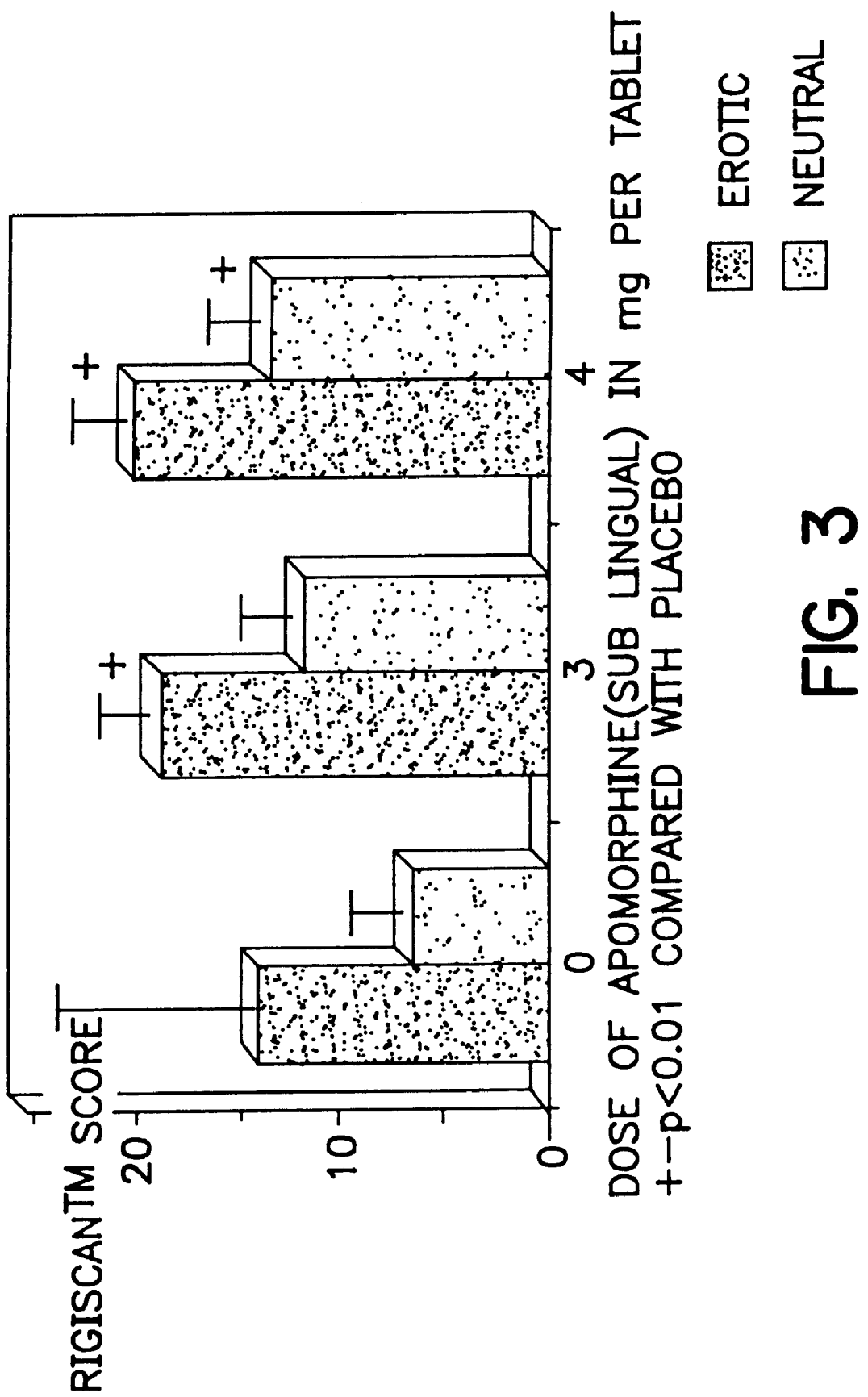
FIG. 3 is a bar graph presenting yet another comparison of erectile function noted in Pilot Study #4 in terms of RIGISCAN™ monitor score versus placebo, 3 milligrams of apomorphine and 4 milligrams of apomorphine under erotic and neutral conditions.

FIG. 2 and Table VIII C show that the statistically significant superiority of active over placebo treatment, regardless of stimulus background, is maintained when the erectile function scores are classified to reflect success (score at least 16) or failure (score less than 16).

TABLE VII

Summary of Results from Pilot Study #4 in Psychogenic Patients

| | | | Apomorphine · HCl Sublingual Tablet | | | | | |
|---|---|---|---|---|---|---|---|---|
| | PLACEBO | | 3 Mg Dose (µg/kg) | | 4 Mg Dose (µg/kg) | | 5 Mg Dose (µg/kg) | |
| Patient #(Wt., kg) | Erotic #1 | Neutral #1 | Erotic #2 | Neutral #2 | Erotic #3 | Neutral #3 | Erotic #4 | Neutral #4 |
| 401 (68.5) | 31 | 28 | 29 (44) | 27 (44) | 33 (58) | 27 (58) | | |
| 402 (70.3) | 12 | 4 | 12 (43) | 4 (43) | 17 (57) | 6 (57) | | |
| 403 (118) | 16 | 4 | 22* (25) | 5 (25) | 22* (34) | 25 (34) | | |
| 404 (83.5) | 24 | 10 | 26* (36) | 17 (36) | 25* (48) | 17 (48) | | |
| 405 (78) | 11 | 1 | 18* (38) | 6 (38) | 12 (51) | 8 (51) | 10 (64) | 5 (64) |
| 406 (80) | 14 | 5 | 18* (38) | 17 (38) | 17* (50) | 2 (50) | | |
| 407 (100) | 8 | 0 | 18* (30) | 4 (30) | 10 (40) | 3 (40) | | |
| 408 (86.2) | 28 | 18 | 32 (35) | 21 (35) | 34 (46) | 22 (46) | | |
| 409 (93) | 2 | 0 | 4 (32) | 1 (32) | 8 (43) | 6 (43) | 5 (54) | 4 (54) |
| 410 (80) | 3 | 0 | 13 (38) | 16 (38) | 8 (50) | 7 (50) | | |
| 411 (98) | 13 | 5 | 26* (31) | 23* (31) | 24* (42) | 20 (42) | | |
| 412 (73) | 7 | 3 | 7 (41) | 1 (41) | 28* (55) | 19* (55) | | |

*Patients with score higher than 16 (see scoring table) are positive respondents.
Out of 12 patients who were treated in this study, 5 showed improvement at both 3 mg and 4 mg doses.
Two (2) showed response only at one dose.
No improvement in clinical response was observed at 5 mg dose.

The data of Pilot Study #4 were analyzed in two ways. First, mean erectile function was compared across placebo, 3 mg and 4 mg doses under two stimulus backgrounds, erotic and neutral. Next erectile function scores were dichotomized, with values less than sixteen considered to reflect erectile insufficiency.

A. Mean Erectile Function

Table VIII A shows means and standard errors for all three treatments under both backgrounds, erotic and neutral. Means were compared using a restricted maximum likelihood generalized linear model containing two main effects, treatment and stimulus, and the treatment by stimulus interaction. An appropriate variance-covariance structure was established for the underlying statistical model using

TABLE VIII A

Mean and Percent Successful Erectile Function

| Stimulus | Treatment | N | Mean (SE) | Percent (SE) |
|---|---|---|---|---|
| Erotic | Placebo | 12 | 14.08 (2.69) | 33.33 (13.61) |
| | 3 mg | 12 | 18.75 (2.51) | 66.67 (13.61) |
| | 4 mg | 12 | 19.83 (2.67) | 66.67 (13.61) |
| Neutral | Placebo | 12 | 6.50 (2.45) | 16.67 (10.76) |
| | 3 mg | 12 | 11.83 (2.68) | 50.00 (14.43) |
| | 4 mg | 12 | 13.50 (2.61) | 50.00 (14.43) |

Note:
Mean (SE) from SAS PROC UNIVARIATE. Percent (SE) from SAS PROC CATMOD.

TABLE VIII B

Anova for Mean Erectile Function

| EFFECT | DF | F | P-value |
|---|---|---|---|
| Treatment | 2.66 | 11.56 | 0.0000 |
| Stimulus | 1.66 | 37.14 | 0.0000 |
| Treatment by Stimulus | 2.66 | 0.10 | 0.9046 |
| Contrasts | | | |
| Erotic: Placebo vs. Treatment | 1.66 | 9.30 | 0.0033 |
| Erotic: 3 mg vs. 4 mg | 1.66 | 0.30 | 0.5849 |
| Neutral: Placebo vs. Treatment | 1.66 | 13.03 | 0.0006 |
| Neutral: 3 mg vs. 4 mg | 1.66 | 0.71 | 0.4014 |

Note:
Restricted maximum likelihood analysis performed using SAS PROC MIXED.

TABLE VIII C

Logistic Regression for Percent Successful Erectile Function

| EFFECT | DF | $X^2$ | P-value |
|---|---|---|---|
| Treatment | 2 | 15.36 | 0.0005 |
| Stimulus | 1 | 5.14 | 0.0233 |
| Treatment by Stimulus | 2 | 0.00 | 1.0000 |
| Contrasts | | | |
| Erotic: Placebo vs. Treatment | 1 | 9.60 | 0.0019 |
| Erotic: 3 mg vs. 4 mg | 1 | 0.00 | 1.0000 |
| Neutral: Placebo vs. Treatment | 1 | 9.60 | 0.0019 |
| Neutral: 3 mg vs. 4 mg | 1 | 0.00 | 1.0000 |

Note:
Analysis performed using SAS PROC CATMOD.

TABLE IX

Visual Analogue Scale (VAS)
(to be completed by the patient)
Please mark each line clearly at the point which indicates how you are feeling right now. Each line represents the full range of each feeling.
(There are no right or wrong answers)

| | | Score (mm) |
|---|---|---|
| 1. | Alert–Drowsy | |
| 2. | Calm–Excited | |
| 3. | Yawning–Not Yawning | |
| 4. | Fuzzy–Clear Headed | |
| 5. | Well Coordinated–Clumsy | |
| 6. | Tired–Energetic | |
| 7. | Contented–Disconnected | |
| 8. | Troubled–Tranquil | |
| 9. | Mentally slow–Quick Witted | |
| 10. | Tense–Relaxed | |
| 11. | Attentive–Dreamy | |
| 12. | Stomach Upset–Feeling Well | |
| 13. | Anxious–Carefree | |
| | (measure from left to right) | |

Dose Evaluation Study

Clinical response to sublingual administration of apomorphine was evaluated utilizing a group of 60 non-vasculogenic impotent patients. Each patient had a history of erectile dysfunction for at least 3 months, normal biothesiometry response, and normal cavernosometry results.

The patients were divided into seven groups. Each group received a predetermined dosage of apomorphine for 20 days in the form of apomorphine hydrochloride tablets 20 minutes prior to intercourse. Seven different dosages were evaluated—3 mg, 4 mg, 5 mg, 6 mg, 7 mg, 8 mg and 10 mg. The tablet constituents were those shown in Table I, above.

Assessment of response was made on the basis of the patient's report of his experience. A response was deemed positive when the patient experienced an erection sufficiently rigid to effect penetration. Side effects such as nausea and/or vomiting, if present, were noted as well.

The results of this study are compiled in Table X, below.

TABLE X

Results of Dose Evaluation Study

| No. of Patients | Dosage, mg | Positive Responses No. | Positive Responses % | Nausea No. | Nausea % | Vomiting No. | Vomiting % |
|---|---|---|---|---|---|---|---|
| 5 | 3 | 0 | 0 | 0 | 0 | 0 | 0 |
| 5 | 4 | 2 | 40 | 1 | 20 | 1 | 20 |
| 10 | 5 | 5 | 50 | 2 | 20 | 1 | 10 |
| 10 | 6 | 7 | 70 | 2 | 20 | 2 | 20 |
| 10 | 7 | 7 | 70 | 2 | 20 | 2 | 20 |
| 10 | 8 | 7 | 70 | 3 | 30 | 3 | 30 |
| 10 | 10 | 8 | 80 | 4 | 40 | 4 | 40 |

From the foregoing Table it can be seen that at a 4-mg dosage 40 percent of patients had a positive response, at a 5-mg dosage 50 percent of patients had a positive response, at 6-mg, 7-mg, and 8-mg dosages 70 percent of patients had a positive response and at a 10-mg dosage 80 percent of patients had a positive response. However, the incidence of side effects increased as well as the dosage was increased.

The aforesaid apomorphine dosage forms are also well suited for diagnosing male human patients suffering from male erectile dysfunction. For diagnostic purposes, at least about 3 milligrams of apomorphine are administered sublingually to the patient and the patient is exposed to a visual erotic stimulus, e.g., an erotic videotape, while the patient's response thereto is monitored. If deemed desirable for diagnostic purposes, up to about 10 milligrams of apomorphine can be administered to the patient.

In particular, the patient's maximum increase in penile circumference (preferably tip as well as basal) is determined and the patient's maximum penile rigidity (preferably tip as well as basal) is determined. The determined circumferential increase and rigidity values are then compared against a predetermined base value. Equivalent methods of determining tumescence and rigidity can also be utilized.

Pilot Study #5

A clinical study, "Absorption and pharmacokinetic evaluation of apomorphine after sublingual and intravenous routes of administration" compared the absorption and pharmacokinetic profile of apomorphine administered intravenously and slowly at a 1 mg dose with apomorphine sublingual tablets at doses of 4 mg (Table I) and 8 mg administered on 3 occasions, 4 days apart, over a 12 day period in a cross-over study design. The tolerance for apomorphine for each route and each dose administered was determined.

The study was conducted as an open-label, single center, 3-way crossover design. The study population was seven healthy, Caucasian male volunteers between 18 and 35 years of age. A 15-day pre-study evaluation period was followed by a 12-day active treatment phase. Three doses (one intravenous; 2 sublingual) were administered to each subject in random order 4 days apart. A total of 36 serum samples were obtained from each subject at the following time periods: 0, 2, 3, 5, 10, 20, 30 and 45 minutes; and 1, 2, 3, 4 and 6 hours post dose administration.

Safety was assessed within 15 days prior to study start and within one week after the last dose was administered.

General physical examination was performed. Change from baseline in vital signs, height/weight measurements, ECG, orthostatic arterial pressures, heart rate, serum chemistry profile, hematology profile and urinalysis were recorded. Adverse experiences were recorded at each visit and tabulated.

Data Analysis

1. Pharmacokinetic Analysis

Pharmacokinetic analysis was performed by compartmental and noncompartmental methods described below. Nonlinear, iterative, least-squares regression analysis was performed with the computer program, PPHARM (Simed Co., Philadelphia, Pa.).

A. Compartmental Analysis

The apomorphine plasma concentration data for each subject following intravenous administration was fitted to two-compartment open model with a first order input function as described by the following equations.

Plasma apomorphine concentration was described for intravenous administration data by equation (1):

$$C_t = Ae^{-\alpha t} + Be^{-\beta t} \quad (1)$$

Plasma apomorphine concentration was described for sublingual tablet administration by equations (2) and (3):

$$C_t = \frac{FDk_a}{V_d(k_a - k_e)}\left(e^{-k_e(t-t_{lag})} - e^{-k_a(t-t_{lag})}\right) \quad (2)$$

$$C_t = Ae^{-\alpha(t-t_{lag})} + Be^{-\beta(t-t_{lag})} + Ce^{-k_a(t-t_{lag})} \quad (3)$$

In the above equations, $C_t$ is the apomorphine plasma concentration at time t; F is the relative bioavailability, which is assumed to be one for intravenous administration; $K_a$ is the first order rate constant for sublingual absorption; $K_e$ is the first order rate constant for elimination; $V_d$ is the volume of distribution; D is the apomorphine dose; t is time; $t_{lag}$ is the lag time before onset of sublingual absorption; A, B, C are the intercepts of the distribution, elimination, and absorption phases, respectively; $\alpha$ is the distribution rate constant; $\beta$ is the elimination rate constant; and $K_a$ is the absorption rate constant.

Initial estimates of the intravenous and sublingual pharmacokinetic parameters were obtained with the computer program PPHARM (Simed Co., Philadelphia, Pa.). These initial estimates were used to fit the data to equations (1), (2) and (3) by nonlinear iterative least squares regression analysis. The results are shown graphically in FIG. 4. The estimate of F (relative bioavailability) for sublingual administration was obtained from the noncompartmental analysis outlined below.

Visual inspection of the fitted curves, analysis of the residual plots, the Akaike information criterion, and correlation coefficients between observed and calculated values were used to select the appropriate pharmacokinetic model for each set of plasma concentration versus time data. A weighting factor was used to fit the data.

The regression analysis provided the final estimates of the pharmacokinetic parameters: $V_d$, $K_e$, $K_a$, and $t_{lag}$ from equation (2), and A, B, C, $\alpha$, $\beta$, $k_a$, and $t_{lag}$ from equation (3). The maximum plasma concentration ($C_{max}$), time to maximum plasma concentration ($T_{max}$), and $V_d$ (volume of distribution) were calculated using standard compartmental pharmacokinetic equations (Gibaldi, M. & Perrier, D. *Pharmacokinetics*, 2d edition, Marcel Dekker, Inc. New York, 1982).

The values for $C_{max}$ and $T_{max}$ obtained by visual inspection of the plasma concentration versus time curve were reported for comparative purposes. Model dependent and independent pharmacokinetic parameters (presented in Tables XI–XIV) were calculated for each patient using the best fit of Equation (3) to the data.

B. Noncompartmental Analysis

The area under the curve, $AUC_{o-inf}$, was determined by adding the $AUC_{o-last}$ to the $AUC_{t-last}$, where $AUC_{t-last} = C_t / R_e$, $C_t$ is the plasma concentration at time$^t$, and $R_e$ is $K_e$ the first order rate constant for elimination.

If the plasma concentration versus time data for a subject could not be adequately fit to equation (1), (2) or (3), the $K_e$ was determined by linear regression analysis of the log plasma concentration regression analysis of the log plasma concentration versus time during the post-absorption phase. Estimates of noncompartmental parameters $C_{max}$ and $T_{max}$ were obtained from visual inspection of the plasma concentration time curves.

The relative bioavailability (F) for a sublingual dose was calculated by the following equation:

$$F = \frac{AUC_{SL} * D_{IV}}{AUC_{IV} * D_{SL}} \quad (4)$$

2. Statistical Analysis

An analysis of variance (ANOVA) for a three-way crossover study design was utilized to compare the pharmacokinetic parameters (AUC, $C_{max}$, and $t_{lag}$) determined as described above for the intravenous administration at 1 mg dose and those determined for the sublingual administration of apomorphine at the 4 mg and the 8 mg doses. The ANOVA was tested for the presence of any period or residual carryover effects in the data. Statistical significance was set at an alpha level equal to 0.05. The ability of the ANOVA to detect both a 20% difference and the observed difference between the sublingual and intravenous pharmacokinetic parameters was determined. In addition to the ANOVA, the 95% confidence interval of the percent difference between the sublingual and SC parameters was calculated from the error variance and degrees of freedom of the ANOVA model.

The data were summarized as the mean±standard deviation in Tables XI–XIV below.

TABLE XI

NONCOMPARTMENTAL PHARMACOLOGIC PARAMETERS
(MEAN ± SD) AND RANGE

| Parameter | IV Administration | | | | 4 mg Dose | | | | 8 mg Dose | | | |
| --- | --- | --- | --- | --- | --- | --- | --- | --- | --- | --- | --- | --- |
| | Mean | ±SD | Low | High | Mean | ±SD | Low | High | Mean | ±SD | Low | High |
| Ke (min$^{-1}$) | 0.0237 | 0.0140 | 0.0091 | 0.0432 | 0.0156 | 0.0138 | 0.0038 | 0.0336 | 0.0056 | 0.0036 | 0.00222 | 0.0102 |
| T$_{1/2}$ (min) | 39.44 | 0.219 | 16.04 | 76.49 | 89.18 | 75.43 | 20.62 | 183.60 | 176.30 | 112.30 | 68.09 | 314.6 |

TABLE XI-continued

NONCOMPARTMENTAL PHARMACOLOGIC PARAMETERS (MEAN ± SD) AND RANGE

| Parameter | IV Administration | | | | 4 mg Dose | | | | 8 mg Dose | | | |
|---|---|---|---|---|---|---|---|---|---|---|---|---|
| | Mean | ±SD | Low | High | Mean | ±SD | Low | High | Mean | ±SD | Low | High |
| Tmax (min) | 2.286 | 1.254 | 1.000 | 5.000 | 17.50 | 18.48 | 5.000 | 45.00 | 52.50 | 85.10 | 5.000 | 15.00 |
| Cmax (min) | 8.364 | 3.886 | 3.400 | 12.90 | 0.8375 | 0.6848 | 0.3000 | 0.8500 | 2.069 | 2.366 | 0.5750 | 1.150 |
| AUC (0-inf) (min*ng/ml) | 206.9 | 45.47 | 140.8 | 260.1 | 31.64 | 18.62 | 10.13 | 55.55 | 339.9 | 459.2 | 15.00 | 316.6 |
| Cl (ml/min) | 0.0051 | 0.0012 | 0.0038 | 0.0071 | 0.0456 | 0.0361 | 0.0180 | 0.0988 | 0.2056 | 0.2460 | 0.0253 | 0.5333 |
| Vd (beta) (ml) | 0.2344 | 0.1532 | 0.0056 | 0.4982 | 4.076 | 2.053 | 1.017 | 5.277 | 69.09 | 115.80 | 7.932 | 64.27 |
| Vd (SS) (ml) | 0.1942 | 0.0817 | 0.1357 | 0.3401 | 1.836 | 0.7112 | 0.999 | 2.475 | 46.30 | 74.46 | 6.523 | 12.42 |
| MRT (min) | 40.29 | 18.90 | 20.14 | 75.32 | 64.25 | 55.14 | 15.12 | 137.5 | 143.7 | 148.0 | 23.29 | 329.3 |
| F° (% Relative Bioavailability) | — | — | | | 0.04 | (4.0%) | | | 0.21 | (21%) | | |
| F° = (AUC$_{SL}$*DOSE$_{IV}$)/(AUC$_{IV}$*DOSE$_{SL}$) | | | | | | | | | | | | |

Cl = clearance
Vd = volume of distribution @ β stage.
Vd (SS) = volume of distribution steady state
MRT = means residual time

TABLE XII

Noncompartmental Pharmacokinetic Parameters (Mean ± SD) for IV Administration (1 mg)
n = 7

| | Subject | | | | Subject | | | Range | | | |
|---|---|---|---|---|---|---|---|---|---|---|---|
| | #1 | #2 | #3 | #4 | #5 | #6 | #7 | Mean | ±SD | Low | High |
| Ke (/min) | 0.0432 | 0.0129 | 0.0091 | 0.0419 | 0.0168 | 0.0150 | 0.0268 | 0.0237 | 0.0140 | 0.0091 | 0.0432 |
| T$_{1/2}$ (min) | 16.04 | 53.79 | 76.49 | 16.56 | 41.22 | 46.18 | 25.84 | 39.44 | 21.92 | 16.04 | 76.49 |
| Tmax (min) | 2.000 | 2.000 | 2.000 | 2.000 | 2.000 | 5.000 | 1.000 | 2.286 | 1.254 | 1.000 | 5.000 |
| Cmax (ng/ml) | 8.400 | 11.200 | 4.150 | 12.250 | 12.900 | 3.400 | 6.250 | 8.364 | 3.886 | 3.400 | 12.900 |
| AUC (O-inf) (min*ng/ml) | 140.8 | 255.4 | 221.5 | 177.1 | 224.6 | 169.0 | 260.1 | 206.9 | 45.47 | 140.8 | 260.1 |
| Cl (ml/min) | 0.0071 | 0.0039 | 0.0045 | 0.0056 | 0.0045 | 0.0059 | 0.0038 | 0.0051 | 0.0012 | 0.0038 | 0.0071 |
| Vd (beta) (ml) | 0.1643 | 0.3039 | 0.4982 | 0.0056 | 0.2648 | 0.2574 | 0.1466 | 0.2344 | 0.1532 | 0.0056 | 0.4982 |
| Vd (SS) (ml) | 0.1430 | 0.1512 | 0.3401 | 0.1147 | 0.2174 | 0.2574 | 0.1357 | 0.1942 | 0.0817 | 0.1357 | 0.3401 |
| MRT (min) | 20.14 | 38.62 | 75.32 | 20.32 | 48.82 | 43.50 | 35.31 | 40.29 | 18.90 | 20.14 | 75.32 |

TABLE XIII

Noncompartmental Pharmacokinetic Parameters (Mean ± SD) for Sublingual Administration (4 mg Dose)
n = 4

| | Subjects | | | | Range | | | |
|---|---|---|---|---|---|---|---|---|
| | #1 | #3 | #6 | #7 | Mean | ±SD | Low | High |
| Ke (/min) | 0.0188 | 0.0336 | 0.0060 | 0.0038 | 0.0156 | 0.0138 | 0.0038 | 0.0336 |
| T$_{1/2}$ (min) | 36.78 | 20.62 | 115.7 | 183.6 | 89.18 | 75.43 | 20.62 | 183.6 |
| Tmax (min) | 10.00 | 10.00 | 5.000 | 45.00 | 17.50 | 18.48 | 5.000 | 45.00 |
| Cmax (ng/ml) | 0.8500 | 1.8000 | 0.3000 | 0.4000 | 0.8375 | 0.6848 | 0.3000 | 0.8500 |
| AUC (O-inf) (min*ng/ml) | 10.13 | 29.25 | 31.64 | 55.55 | 31.64 | 18.62 | 10.13 | 55.55 |
| Cl (ml/min) | 0.0988 | 0.0342 | 0.0316 | 0.0180 | 0.0456 | 0.0361 | 0.0180 | 0.0988 |
| Vd (beta) (ml) | 5.241 | 1.017 | 5.277 | 4.769 | 4.076 | 2.053 | 1.017 | 5.277 |
| Vd (SS) (ml) | 1.494 | 0.999 | 2.377 | 2.475 | 1.836 | 0.7112 | 0.999 | 2.475 |
| MRT (min) | 15.12 | 29.23 | 75.19 | 137.47 | 64.25 | 55.14 | 15.12 | 137.47 |

TABLE XIV

Noncompartmental Pharmacokinetic Parameters (Mean ± SD)
for Sublingual Administration (8 mg Dose)
n = 4

| | Subjects | | | | Range | | | |
|---|---|---|---|---|---|---|---|---|
| | #2 | #3 | #4 | #6 | Mean | ±SD | Low | High |
| Ke (/min) | 0.0067 | 0.0032 | 0.0120 | 0.0022 | 0.0056 | 0.0036 | 0.0022 | 0.0102 |
| $T_{1/2}$ (min) | 104.0 | 218.4 | 68.09 | 314.6 | 176.3 | 112.3 | 68.09 | 314.6 |
| Tmax (min) | 180.0 | 10.00 | 15.00 | 5.000 | 52.50 | 85.10 | 5.000 | 180.0 |
| Cmax (ng/ml) | 5.600 | 1.150 | 0.9500 | 0.5750 | 2.069 | 2.366 | 0.5750 | 5.600 |
| AUC (O-inf) (min*ng/ml) | 996.6 | 316.6 | 31.25 | 15.00 | 339.9 | 459.2 | 15.00 | 996.6 |
| CL (ml/min) | 0.008 | 0.0253 | 0.2560 | 0.5333 | 0.2056 | 0.2460 | 0.008 | 0.5333 |
| Vd (beta) (ml) | 1.204 | 7.932 | 25.15 | 242.1 | 69.09 | 115.8 | 1.204 | 242.1 |
| Vd (SS) (ml) | 157.9 | 8.320 | 6.523 | 12.42 | 46.30 | 74.46 | 6.523 | 157.9 |
| MRT (min) | 196.7 | 329.3 | 25.48 | 23.29 | 143.7 | 148.0 | 23.29 | 329.3 |

TABLE XV

Summary of Pharmacokinetic Parameters for Apomorphine HCl in Humans

| | | | PUBLISHED DATA | | | | | | |
|---|---|---|---|---|---|---|---|---|---|
| | THIS STUDY | | Durif, F. et al., Clin. Neuropharm. 16:157–166 (1933) | | | Gancher, S.T., et al. Movement Disorders 6:212–216(1991). | | Montastruc, J.L., et al. Clin. Neuropharmacol. 14:432–437(1991). | |
| ROUTE | i.v. | s.l. | s.l. | s.l. | s.l. | s.l. | s.c. | i.v. | s.l. | s.c. |
| # Subjects | 7 | 7 | 7 | 7 | 7 | 5 | 5 | 5 | 9 | 9 |
| # Tablets × Strength (mg) | n/d | 1 × 4 | 1 × 8 | 7 × 3 | 14 × 3 | 3 × 6 | n/a | n/a | 10 × 3 | n/a |
| Dose (mg/kg) | 0.01 | 0.06 | 0.114 | 0.3 | 0.6 | 0.25 | 0.02 | 0.038 | 0.42 | 0.04 |
| Cmax (ng/ml) | 8.3 | 0.83 | 2.07 | 7.5 | 22.7 | 14.3 | 19.36 | 31.2 | 28 | 26 |
| $T_{max}$ (min) | 2.2 | 17.5 | 52.5 | 31.5 | 38.3 | 45 | 6.5 | 6.7 | 41 | 18 |
| AUC (min*ng/ml) | 207 | 31.6 | 340 | 929 | 2,277 | 1,057 | 592.7 | 881.1 | 1,882 | 837 |
| Cl (l/hr/kg) | 4.37 | n/d | n/d | 2.1 | 1.8 | n/d | n/d | n/d | n/d | n/d |
| Vd (l/kg) | 3.35 | 2.33 | 2.07 | 3.4 | 2.8 | n/d | n/d | 0.043 | n/d | n/d |
| MRT (min) | 40.3 | 64.2 | 143.7 | 128 | 125 | n/d | n/d | n/d | n/d | n/d |
| $T_{1/2}$ (min) | 39.4 | 89.2 | 176.3 | 72 | 70 | n/d | n/d | n/d | n/d | n/d |
| Bioavailability (F) | n/a | 4% | 21% | 10% | 10% | 17% | n/a | n/a | n/d | n/a | n/d = not done
n/a = not applicable
*Calculated
Clin. Neuropharm. 16:157–166 (1993)

Figure 4:
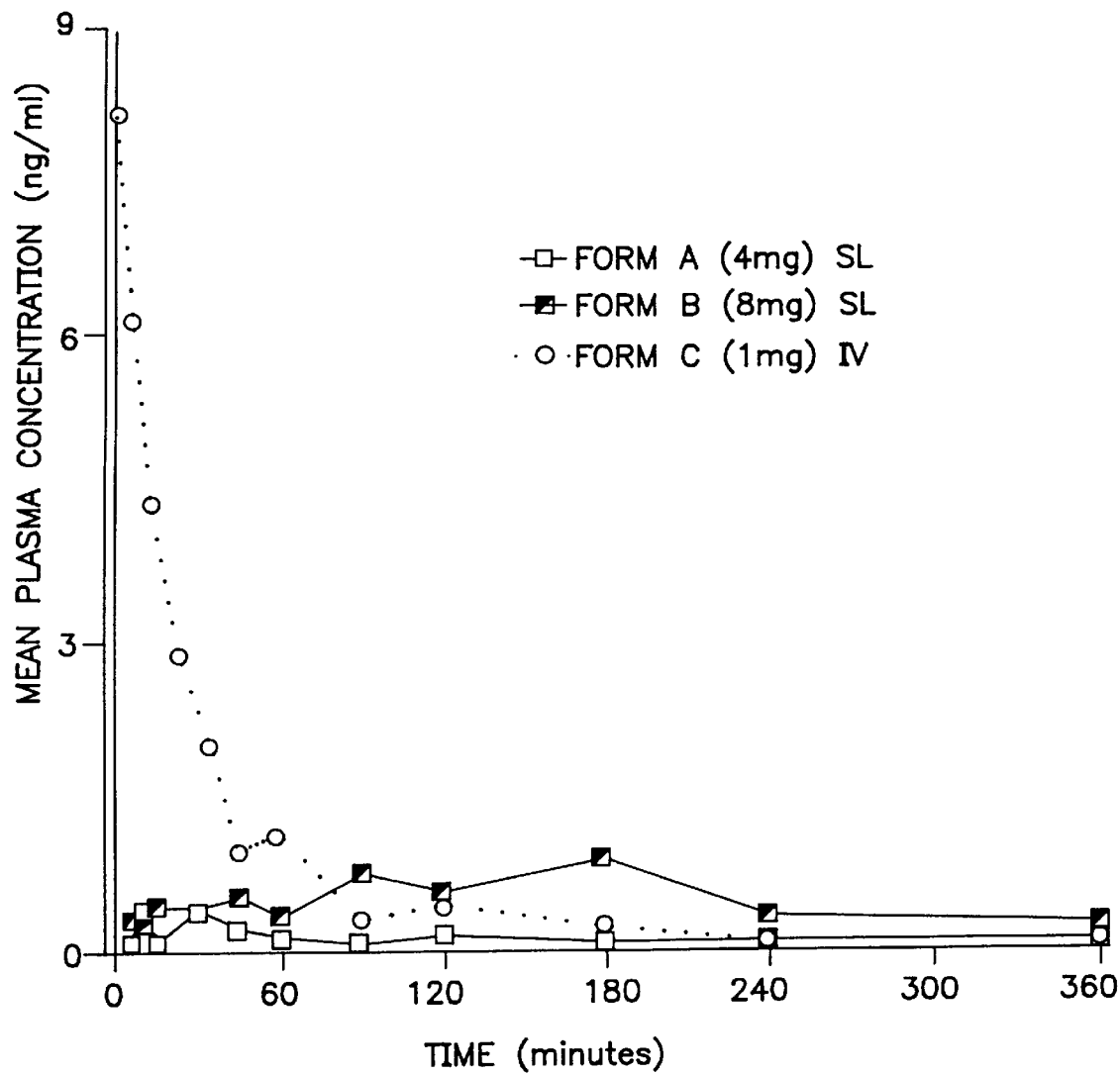
FIG. 4 is a graphical representation of a comparison of the plasma concentration time profiles of apomorphine after intravenous administration at a dose of 1 mg (open circles, n=7), sublingual administration at a dose of 4 mg (open squares, n=4) and sublingual administration at a dose of 8 mg (half-filled squares, n=4)

The results, summarized in Tables XI–XIV above and shown graphically in FIG. 4, show that the plasma concentration of apomorphine drops quickly when the drug is administered intravenously. In contrast, the plasma concentration of apomorphine rises slowly to a lower level when administered sublingually.

The importance of these findings is put into perspective when compared to information on the administration of apomorphine that is available in the literature (Table XV). The sublingual administration of apomorphine by the present invention produced a lower plasma concentration than the administration and dosage regimes listed for previous reports.

Pilot Study #6

A clinical study of patient tolerance of escalating doses in sublingual tablet administration of APO for the treatment of psychogenic male erectile dysfunction was performed. The pilot study compared the effects of sublingual tablet administration of placebo, and 4, 6 and 8 mg apomorphine hydrochloride (APO) on male erectile dysfunction as measured by RIGISCAN™ monitoring and self-reported satisfaction with the treatment results.

The study included 50 men with psychogenic male erectile dysfunction (MED). The study was conducted in three phases. In the first phase, the subject's penile erectile response (measured with the RIGISCAN™ ambulatory tumescence monitor) was evaluated. The subject received a placebo tablet for sublingual administration and then viewed a 30-minute video consisting of two 10-minute erotic sequences separated by a 10-minute neutral sequence. Subjects completed a visual analogue scale questionnaire (VAS, Table VI) about their feelings and well-being.

In the second phase, subjects returned to the clinic for four visits, each visit one week apart. Subjects received one sublingual administration of either placebo, or 4, 6 and 8 mg APO at each visit. Doses of APO were administered in ascending order with the placebo being randomly assigned for use at one of the four visits. The procedures performed before and after drug administration were the same as those in the first phase. After completion of the fourth visit, the investigator determined for each subject the most effective and well-tolerated APO dose for home use in the third phase of the study.

The third phase, a home-use phase, lasted 5 weeks. During this phase, subjects attempted coitus at least once each week after taking a single APO tablet. After each attempt the subject and his partner completed a Sexual Function questionnaire (Table XVI). Subjects had a final evaluation at the end of the 5-week, home-use phase.

Fifty males with psychogenic MED were enrolled in this three phase trial. The first aim of this study was to determine the safety and tolerance of APO in the treatment of MED. Several adverse events directly linked with administration of APO in humans were expected: yawning, nausea, vomiting, and cardiovascular effects. Indeed, nausea was the primary adverse event reported in this trial with an overall incidence of less than 13% of the subjects for all administered doses and only two cases were considered severe. The incidence of vomiting was less than 3% for all administered doses.

Hypotension was reported as an adverse event in some subjects in this study, along with bradycardia, dizziness, syncope, and pallor. Only single cases of hypotension and pallor were judged severe in this study. Increased sweating and fatigue were also reported. One of the cases of increased sweating was considered severe. The other severe adverse events (mouth edema, dysphagia, upper respiratory tract infection) were judged unrelated to treatment.

Changes in the serum chemistry values and vital signs paralleled the adverse event reports. There were no clinically significant changes except for one subject judged to have abnormal liver function of unknown origin. There were no clinically significant changes in the blood or urinalysis values due to drug.

The efficacy of APO was evaluated during the first two phases of the study in which subjects were attached to the RIGISCAN™ monitor. Subjects were initially treated with placebo in the first phase. In the second phase, patients received 4, 6 and 8 mg APO tablets with a placebo tablet randomly interspersed in the treatment.

There were highly significant effects of APO treatment compared to placebo. These observations indicate that APO has effects on penile function in both erotic and neutral environments (Tables XVII–XIX). All summed scores showed significant treatment effects at one or more of the three doses of APO. The overall RIGISCAN™ score results were significant to highly significant for a treatment effect of 4, 6 and 8 mg compared to the initial placebo. In addition, most of the treatment effects were significant to highly significant compared to the second placebo.

The effects in the erotic video sequences were larger than the effects in the neutral video sequence (TABLES XVII–XIX). Effects in erotic video sequence one were larger than the effects in erotic video sequence two (TABLE XVII). More significant treatment effects were seen in response to the neutral video sequence, but this reflects the larger number of subjects in this data subset, as one center did not show the erotic video sequences. All doses of APO were effective in causing erections (RIGISCAN™ reading ≧15 in the presence of erotic stimulation; TABLE XVII).

During the third phase, subjects had recorded at baseline, their satisfaction, erection, number of attempts, and successful intercourse on a VAS scale. Evaluable subjects first recorded a success rate, then completed VAS for erection results and satisfaction with intercourse following take-home treatment. Success rate was calculated for mg as well as µg/kg body weight doses (males). Several evaluations of the data were made including the male and female responses to treatments. The overall average success rate is 69% with APO treatment which is much higher than the average baseline rate 28% (Tables XX, XXI).

The success rate showed numerical increase at tablet strength from 4 mg to 6 mg, but a decrease at 8 mg (TABLE XX). The highest success rate was 73% in both males and females at a tablet strength of 6 mg (TABLE XX). When the dosage is examined as a function of body weight, a dosage range of 50–74 µg/kg gave the highest success rate(: 82%) in females and (80%) in males (Table XXI). The dosage range of 35–50 µg/kg gave the highest success rate.

The optimal response was observed with 4 or 6 mg APO sublingual tablets which caused erections in the majority (72%) of men with male erectile dysfunction (MED) with few severe adverse effects.

TABLE XVI

SEXUAL FUNCTION STUDY HOME QUESTIONNAIRE-Male
Please answer questions within 12–24 hours of taking sublingual tablet.

Initials:_____ Subject#:_____ Today's Date:_____ Time: _____
Date Tablet Taken:_____ Time: _____

The lines below represent the full range of feeling or response. Please mark each line clearly with a vertical (straight up and down) stroke at the point which represents your response. (There are no right or wrong answers. Do not write in boxes on right.)

1. What was your erection result after taking the sublingual tablet?

No Erection_____ Rigid Erection Suitable for Penetration [ ]

2. Did you have intercourse with  [ ] Yes  [ ] No
   wife/partner after taking tablet?

IF NO. please       0-No erection.
   circle all reasons  1-Erection not sufficient for penetration.
   that apply:         2-Felt sick after taking tablet. (Describe below in #4.)
                       3-I decided not to participate in intercourse.
                       4-Wife/partner decided not to participate.
                       5-Uurelated interruption (example, telephone call).
                       6-Wife/partner menstruating.
                       7-Other, explain:_____

3. What was your level of satisfaction with this attempt at sexual intercourse?

Extremely Unsatisfied_____ Extremely Satisfied [ ]

4. Please describe any adverse reactions you experienced after taking the sublingnal tablet. (Indicate when the reaction started and stopped, and any intervention taken i.e. "nosebleed on 5/1/94, used a cold compress".)
   _____
   _____
   _____

5. Other comments?_____
   _____

TABLE XVII

Total RIGISCAN ™ Scores by Phase
Mean ± SEM

|  | Phase I | Phase II | | | |
|---|---|---|---|---|---|
| Video | Placebo 1 | Placebo 2 | 4 mg | 6 mg | 8 mg |
| Erotic 1<br>N = 31–36 | 11.44 ± 1.77 | 13.38 ± 2.05 | 15.31 ± 1.76* | 17.09 ± 1.64** | 19.84 ± 1.61** |
| Erotic 2<br>N = 29–36 | 11.39 ± 1.70 | 13.31 ± 1.88 | 15.26 ± 1.72* | 16.44 ± 1.98* | 17.79 ± 1.96** |
| Neutral<br>N = 41–48 | 7.98 ± 1.24 | 7.49 ± 1.26 | 11.11 ± 1.30** | 12.76 ± 1.12** | 11.98 ± 1.37** |
|  |  | Corresponding p-values (placebI 1/placebo 2) | | | |
| Erotic 1 | — | 0.3274 | 0.0120 | 0.0007 | 0.0001 |
|  | — | — | 0.1405 | 0.0166 | 0.0005 |
| Erotic 2 | — | 0.4013 | 0.0276 | 0.0196 | 0.0007 |
|  | — | — | 0.1907 | 0.1365 | 0.0091 |
| Neutral | — | 0.6243 | 0.0230 | 0.0009 | 0.0060 |
|  | — | — | 0.0074 | 0.0002 | 0.0017 |

*Significantly higher than placebo 1
**Significantly higher than placebo 1 and placebo 2

TABLE XVIII

Penile Measurements (Maximum Increases Measured by RIGISCAN ™), Erotic Video Sequence #1
Repeated Measures Analysis of Variance

| Site | Treatment Source | DESCRIPTIVE STATISTICS | | | ADJUSTED | | ANALYSIS OF VARIANCE | |
|---|---|---|---|---|---|---|---|---|
|  |  | N | MEAN p-value | SEM | (LS) MEAN LSMEAN | SEM |  |  |
| ALL SITES | Placebo #1 | 36 | 11.44 | 1.770 | 12.22 | 1.666 | Treatment | 0.0001* |
|  | Placebo #2 | 32 | 13.38 | 2.051 | 13.65 | 1.714 | Site | 0.0264* |
|  | 4 mg | 35 | 15.31 | 1.761 | 15.80 | 1.674 | Treatment by Site | 0.0595 |
|  | 6 mg | 34 | 17.09 | 1.841 | 17.20 | 1.695 | 4 mg vs Placebo #1 | 0.0120* |
|  | 8 mg | 31 | 19.84 | 1.610 | 19.11 | 1.745 | 6 mg vs Placebo #1 | 0.0007* |
| SITE #1 | ALL TREATMENTS | 11 | 10.76 | 2.372 | 11.04 | 2.498 | 8 mg vs Placebo #1 | 0.0001* |
|  | Placebo #1 | 11 | 9.73 | 2.854 | 9.73 | 2.931 | 4 mg vs Placebo #2 | 0.1504 |
|  | Placebo #2 | 10 | 9.00 | 3.300 | 9.21 | 2.996 | 6 mg vs Placebo #2 | 0.0166* |
|  | 4 mg | 11 | 8.09 | 2.410 | 8.09 | 2.931 | 8 mg vs Placebo #2 | 0.0005* |
|  | 6 mg | 11 | 10.82 | 3.065 | 10.82 | 2.931 | Placebo #1 vs. #2 | 0.3274 |
|  | 8 mg | 9 | 17.89 | 2.988 | 17.36 | 3.070 |  |  |
| SITE #2 | ALL TREATMENTS | 16 | 13.89 | 1.942 | 14.25 | 2.083 |  |  |
|  | Placebo #1 | 16 | 8.94 | 2.233 | 8.94 | 2.430 |  |  |
|  | Placebo #2 | 14 | 11.71 | 2.768 | 11.38 | 2.515 |  |  |
|  | 4 mg | 15 | 15.27 | 2.379 | 15.10 | 2.476 |  |  |
|  | 6 mg | 15 | 17.60 | 2.267 | 17.43 | 2.476 |  |  |
|  | 8 mg | 15 | 18.60 | 2.265 | 18.43 | 2.476 |  |  |
| SITE #4 | ALL TREATMENTS | 9 | 21.21 | 3.437 | 21.49 | 2.776 |  |  |
|  | Placebo #1 | 9 | 18.00 | 4.304 | 18.00 | 3.240 |  |  |
|  | Placebo #2 | 8 | 21.75 | 4.242 | 20.36 | 3.337 |  |  |
|  | 4 mg | 9 | 24.22 | 2.837 | 24.22 | 3.240 |  |  |
|  | 6 mg | 8 | 24.75 | 3.740 | 23.36 | 3.337 |  |  |
|  | 8 mg | 7 | 25.00 | 3.259 | 21.52 | 3.444 |  |  |

TABLE XIX

Penile Measurements (Maximum Increases Measured by RIGISCAN ™ ), Neutral Video Sequence
Repeated Measures Analysis of Variance

| Site | Treatment Source | N | DESCRIPTIVE STATISTICS MEAN p-value | SEM | ADJUSTED (LS) MEAN LSMEAN | SEM | ANALYSIS OF VARIANCE | |
|---|---|---|---|---|---|---|---|---|
| ALL SITES | Placebo #1 | 48 | 7.98 | 1.236 | 8.34 | 1.220 | Treatment | 0.0002* |
| | Placebo #2 | 43 | 7.49 | 1.257 | 7.65 | 1.272 | Site | 0.1092 |
| | 4 mg | 47 | 11.11 | 1.295 | 11.47 | 1.226 | Treatment by Site | 0.7176 |
| | 6 mg | 45 | 12.76 | 1.116 | 13.10 | 1.268 | 4 mg vs Placebo #1 | 0.0230* |
| | 8 mg | 41 | 11.98 | 1.366 | 12.40 | 1.331 | 6 mg vs Placebo #1 | 0.0009* |
| SITE #1 | ALL TREATMENTS | 11 | 10.56 | 1.987 | 10.70 | 1.789 | 8 mg vs Placebo #1 | 0.0060* |
| | Placebo #1 | 11 | 8.91 | 2.470 | 8.91 | 2.494 | 4 mg vs Placebo #2 | 0.0074* |
| | Placebo #2 | 10 | 5.60 | 2.574 | 5.68 | 2.587 | 6 mg vs Placebo #2 | 0.0002* |
| | 4 mg | 11 | 10.45 | 1.965 | 10.45 | 2.494 | 8 mg vs Placebo #2 | 0.0017* |
| | 6 mg | 11 | 12.73 | 2.832 | 12.73 | 2.494 | Placebo #1 vs. #2 | 0.6243 |
| | 8 mg | 9 | 16.22 | 3.099 | 15.73 | 2.692 | | |
| SITE #2 | ALL TREATMENTS | 16 | 7.02 | 1.192 | 7.22 | 1.495 | | |
| | Placebo #1 | 16 | 4.44 | 1.554 | 4.44 | 2.068 | | |
| | Placebo #2 | 14 | 5.86 | 2.099 | 5.71 | 2.182 | | |
| | 4 mg | 15 | 8.73 | 2.610 | 8.70 | 2.126 | | |
| | 6 mg | 15 | 9.60 | 1.514 | 9.56 | 2.126 | | |
| | 8 mg | 15 | 7.73 | 1.694 | 7.70 | 2.126 | | |
| SITE #3 | ALL TREATMENTS | 12 | 12.22 | 1.476 | 12.09 | 1.706 | | |
| | Placebo #1 | 12 | 11.33 | 2.244 | 11.33 | 2.388 | | |
| | Placebo #2 | 11 | 10.00 | 1.902 | 10.64 | 2.469 | | |
| | 4 mg | 12 | 11.83 | 2.564 | 11.83 | 2.388 | | |
| | 6 mg | 12 | 13.58 | 1.794 | 13.58 | 2.388 | | |
| | 8 mg | 11 | 12.45 | 2.458 | 13.07 | 2.469 | | |
| SITE #4 | ALL TREATMENTS | 9 | 11.63 | 2.864 | 12.35 | 2.023 | | |
| | Placebo #1 | 9 | 8.67 | 4.052 | 8.67 | 2.758 | | |
| | Placebo #2 | 8 | 9.25 | 3.990 | 8.58 | 2.891 | | |
| | 4 mg | 9 | 14.89 | 3.071 | 14.89 | 2.758 | | |
| | 6 mg | 7 | 18.14 | 2.747 | 16.51 | 3.046 | | |
| | 8 mg | 6 | 15.33 | 4.462 | 13.11 | 3.236 | | |

TABLE XX

Reported Success by Tablet Strength

| Group | 4 mg | 6 mg | 8 mg | Overall |
|---|---|---|---|---|
| Female | 5/7 (71.4%) | 11/15 (73.3%) | 4/7 (57.1%) | 20/29 (69.0%) |
| Male | 5/7 (71.4%) | 11/15 (73.3%) | 4/7 (57.1%) | 20/29 (69.0%) |

TABLE XXI

Reported Success by Apomorphine Dosage (µg/kg)

| Group | 35–50 µg/kg | 59–74 µg/kg | >74 µg/kg | Overall |
|---|---|---|---|---|
| Female | 3/5 (60.0%) | 9/11 (81.8%) | 8/13 (61.5%) | 20/29 (69.0%) |
| Male | 4/5 (80.0%) | 8/11 (72.7%) | 8/13 (61.5%) | 20/29 (69.0%) |

Subject Evaluability Rules for Take-home Part
1. Subjects who get one out of two successful intercourse is considered a success [based on subject's answers to the take-home questionaires].
2. Subjects who tried the study medication at home, for at least two times.
3. Subjects who attempted to try a lower or higher does of the original take-home does did not produce opthnum results in combination with anti-nausea agents.
4. Subjects [and partners] who filled out and returned take-home questionnaires.

The practice of the present invention is demonstrated in the following examples. These examples are meant to illustrate the invention rather than to limit its scope. Variations in the treating compositions which do not adversely affect the effectiveness of the apomorphine or the antiemetic agent will be evident to one skilled in the art, and are within the scope of this invention.

EXAMPLE 1

Apomorphine/Nicotine Combination by Wet Granulation Technique—Composition A

Composition A Tablets were prepared from the ingredients listed in Table XXII (below). Each ingredient was weighed as indicated and passed through a #35 mesh screen (sieve opening of about 0.51 mm) to ensure granulation. A solution containing the apomorphine HCL, the citric acid, half the acesulfame-K, half the peppermint flavor and half the chocolate flavor was prepared by dissolving the ingredients into a mixture of equal volumes of purified water and ethanol, USP. The solution was mixed until clear, and then absorbed into the listed amount of microcrystalline cellulose (Avicel 302). The resulting wet mass, which will be labelled "Part A," was mixed in a porcelain dish at room temperature (20° C.) for 30 minutes, and then partially dried to obtain a solid mass. The mass was next granulated by screening through a #50 mesh (ASTM)(sieve opening of about 0.297 mm) stainless steel screen. The wet granules were dried at about 60° C. to 70° C. for about 1 to 1.5 hours. The resulting dried granules were then passed through a #35 mesh screen (sieve opening of about 0.51 mm).

TABLE XXII

Apomorphine/Nicotine Combination Tablet Composition

| Ingredient | mg/tablet |
|---|---|
| Apomorphine HCL | 4.0 |
| Nicotine Base | 1.0 |
| Acesulfame-K | 4.0 |
| Microcrystalline Cellulose | 37.5 |
| Peppermint flavor | 2.5 |
| Chocolate natural flavor | 2.0 |
| Citric acid | 3.0 |
| Hydroxypropylmethylcellulose | 13.0 |
| Mannitol | 80.0 |
| Magnesium stearate | 3.0 |
| TOTAL | 150.0 |

Separately, nicotine was added to and blended with all the remaining ingredients except for the magnesium stearate. Specifically, the nicotine was added to the second half of the acesulfame-K, half the peppermint flavor, half the chocolate flavor, the hydroxypropylmethylcellulose (methocel E4M, premium), and the mannitol. The resulting blend will be labelled "Part B." Parts A and B were then combined and mixed for about 5 minutes in a V-shaped blender. Next, magnesium stearate was added to the blender and blending continued for about 2 minutes.

The final mix was removed from the blender and fed into a Stoke's single punch tablet press fitted with biconvex 5/16" diameter tooling for tablet preparation. Tablets were prepared at various compressional forces, yielding tablets of different hardness. In general, the harder the tablet the slower the release of the active ingredients therefrom.

For additional discussion on methods for preparing sublingual apomorphine tablets see U.S. Pat. No. 5,624,677 to El-Rashidy et al., which is incorporated here by reference to the extent that it is not inconsistent.

The dissolution of apomorphine and nicotine for Composition A Tablets was measured using a USP Type II apparatus (USP XXIII) stirred at 40 rpm. The dissolution medium was 500 ml of 10 millimolar ammonium phosphate buffer at a pH of 3.0±0.5 at about 37° C. The amount of apomorphine and nicotine released into the medium was detected by measuring absorbance at two different wavelengths, 259 nm and 272 nm, and resolving the following two equations:

$$A_{T259} = (\epsilon^{259}_{apo})(C_{apo})(l) + (\epsilon^{259}_{nic})(C_{nic})(l) \quad (5)$$

$$A_{T272} = (\epsilon^{272}_{apo})(C_{apo})(l) + (\epsilon^{272}_{nic})(C_{nic})(l) \quad (6)$$

In the above equations, $A_{T259}$ is the total absorbance at 259 nanometers (nm); $A_{T272}$ is the total absorbance at 272 nm; $\epsilon^{259}_{apo}$ is the molar absorptivity of apomorphine at 259 nm; $\epsilon^{259}_{nic}$ is the molar absorptivity of nicotine at 259 nm; $\epsilon^{272}_{apo}$ is the molar absorptivity of apomorphine at 272 nm; $\epsilon^{272}_{nic}$ is the molar absorptivity of nicotine at 272 nm; $C_{apo}$ is the molar concentration of apomorphine; $C_{nic}$ is the molar concentration of nicotine; and l is the cell path length.

By solving equations (5) and (6), the molar concentration of apomorphine ($C_{apo}$) and nicotine ($C_{nic}$) can be calculated from total absorbance data ($A_{T259}$ and $A_{T272}$) as follows.

$$C_{apo} = (\epsilon^{272}_{nic}A_{T259} - \epsilon^{259}_{nic}A_{T272})/(\epsilon^{259}_{apo}\epsilon^{272}_{nic} - \epsilon^{272}_{apo}\epsilon^{259}_{nic}) \quad (7)$$

$$C_{nic} = (\epsilon^{272}_{apo}A_{T259} - \epsilon^{259}_{apo}A_{T272})/(\epsilon^{272}_{apo}\epsilon^{259}_{nic} - \epsilon^{259}_{apo}\epsilon^{272}_{nic}) \quad (8)$$

Dissolution kinetic constants ($K_{diss}$) for apomorphine and nicotine were calculated assuming zero-order release kinetics.

Figure 5:
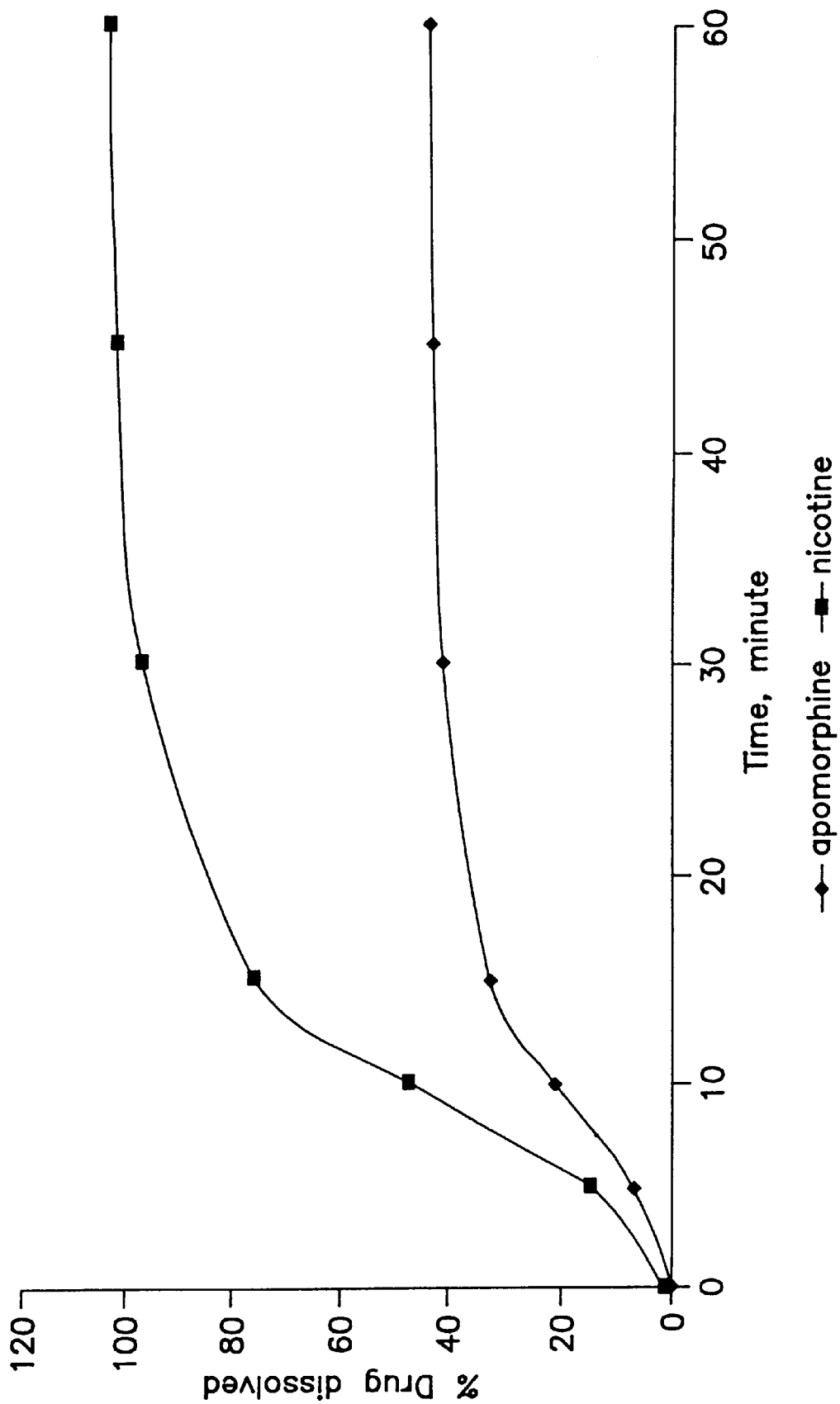
FIG. 5 is a graph of the dissolution pattern of apomorphine and the antiemetic agent nicotine for the tablets of Example 1.

The tablets prepared were compared against a commercially available soluble apomorphine HCl tablet for dissolution characterization. The results are presented in Table XXVI (below) and in FIG. 5. Specifically, the time to 50 percent drug release ($T_{50}$) and 90 percent drug release ($T_{90}$) for both apomorphine and nicotine are reported together with dissolution constants.

In addition, tablet hardness was measured using a Computest Tablet Hardness Tester. These results are also reported in Table XXVI.

Composition A Tablets released apomorphine relatively slower as compared to the release of the antiemetic agent, nicotine.

EXAMPLE 2

Apomorphine/Nicotine Combination by Wet Granulation Technique—Composition B

Composition B Tablets were prepared from the ingredients listed in Table XXII (above). Each ingredient was weighed as indicated and passed through a #35 mesh screen (sieve opening of about 0.51 mm) to ensure granulation. Apomorphine HCL, the hydroxypropylmethyl cellulose, the citric acid, the acesulfame-K, the peppermint flavor, and the chocolate flavor were blended together with the indicated amount of microcrystalline cellulose using 25 percent ethanol in deionized water. The solution was mixed until clear, and then absorbed into half the listed amount of microcrystalline cellulose (Avicel 302). The resulting wet mass (Part A) was mixed in a porcelain mortar at room temperature (20° C.) for about 30 minutes, and then partially dried to obtain a single piece. The mass was granulated using a #35 mesh hand screen (sieve opening of about 0.51 mm). The wet granules were dried at about 60° C. to 70° C. for about 1 to 1.5 hours, and periodically mixed during the drying stage. The resulting dried granules were then passed through a #35 mesh hand screen (sieve opening of about 0.51 mm).

Separately, nicotine was added to and blended with the second half of the microcrystalline cellulose and the mannitol (Part B). Parts A and B were then combined and mixed for about 5 minutes in a V-shaped blender. Next, magnesium stearate was added to the blender, followed by continued blending for about 2 minutes.

The final mix was removed from the blender and compressed into tablets using a Stoke's single punch tablet press fitted with 5/16" diameter biconvex tooling. Tablets were prepared at various compressional forces, yielding tablets of different hardness.

Figure 6:
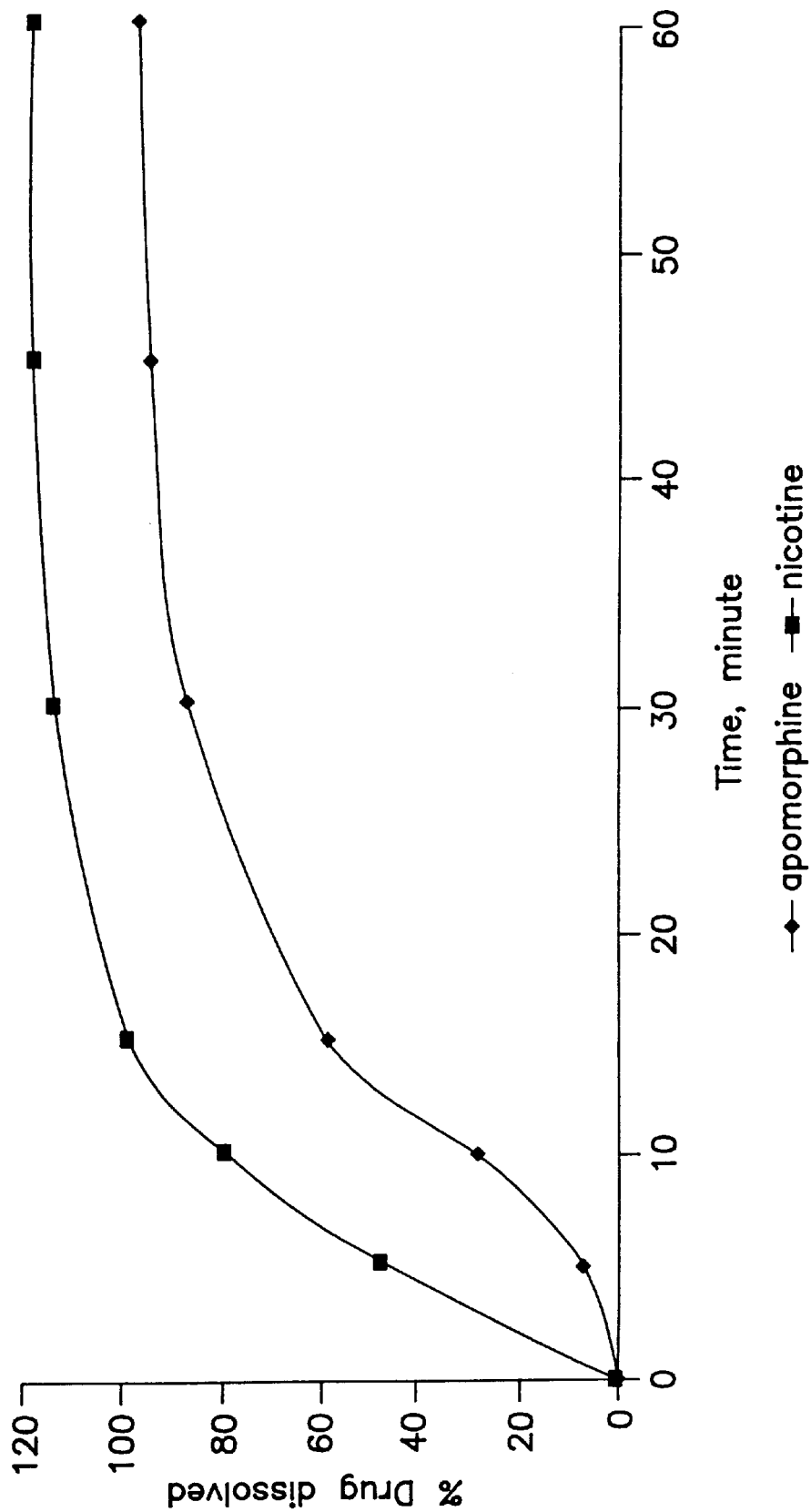
FIG. 6 is a graph of the dissolution pattern of apomorphine and the antiemetic agent nicotine for the tablets of Example 2.

Dissolution of apomorphine and nicotine for Composition B Tablets was measured and reported as described in Example 1. The results are presented in Table XXVI (below) and in FIG. 6. Composition B Tablets released apomorphine relatively slower as compared to the release of nicotine.

EXAMPLE 3

Apomorphine/Nicotine Layered Tablet Combination—Composition C

The ingredients listed in TABLE XXIII (below) were used to prepare a layered tablet having a core portion containing apomorphine HCL and an outer layer containing the antiemetic agent nicotine. All ingredients were first passed through a #35 mesh hand screen (sieve opening of about 0.51 mm).

TABLE XXIII

Apomorphine/Nicotine Layered Tablet Composition

| Ingredient | mg/tablet |
|---|---|
| Tablet core: | |
| Apomorphine HCL | 4.0 |
| Acesulfame-K | 1.6 |
| Microcrystalline Cellulose | 21.6 |
| Peppermint flavor | 1.0 |
| Chocolate flavor | 0.8 |
| Citric acid | 1.2 |
| Hydroxypropylmethylcellulose | 4.0 |
| Mannitol | 24.6 |
| Magnesium stearate | 1.2 |
| Tablet outer layer: | |
| Nicotine base | 1.0 |
| Acesulfame-K | 0.4 |
| Microcrystalline Cellulose | 36.6 |
| Mannitol | 47.0 |
| Magnesium stearate | 1.0 |
| Hydroxypropylmethylcellulose | 4.0 |
| TOTAL | 150.0 |

The core portion was prepared by dry mixing apomorphine HCL, citric acid, peppermint flavor, chocolate flavor and acesulfame-K. The resulting mixture was blended in a V-shaped blender for about 5 minutes. Hydroxypropylmethylcellulose was than added and the blending continued for an additional 5 minutes. The microcrystalline cellulose was then added to the blender and mixing was continued for yet another 5 minutes. Next mannitol was added to the blender, followed by another 5 minute stage of blending. Finally, magnesium stearate was added and blended in for about 2 minutes.

The resulting mixture was transferred to a Stoke's tablet press fitted with 7/32" diameter biconvex tooling to generate tablet cores with a hardness of about 3 kilopascals (Kp).

The outer antiemetic layer was prepared by mixing nicotine with the listed amount of microcrystalline cellulose in a porcelain mortar until the mixture became homogeneous. The homogeneous mixture was then transferred to a V-shaped blender, where the listed amounts of mannitol, hydroxypropylmethylcellulose, and acesulfame-K were blended in for about 5 minutes. Magnesium stearate was then added followed by an additional 2 minutes of blending.

A portion of the nicotine mixture was then transferred to the die of the Stoke's tablet press fitted with 5/16" biconvex tooling. Next an apomorphine tablet core discussed above was placed in the die and then covered with another portion of the nicotine mixture. The nicotine mixture and core portion were finally compressed together to form layered tablets.

Figure 7:
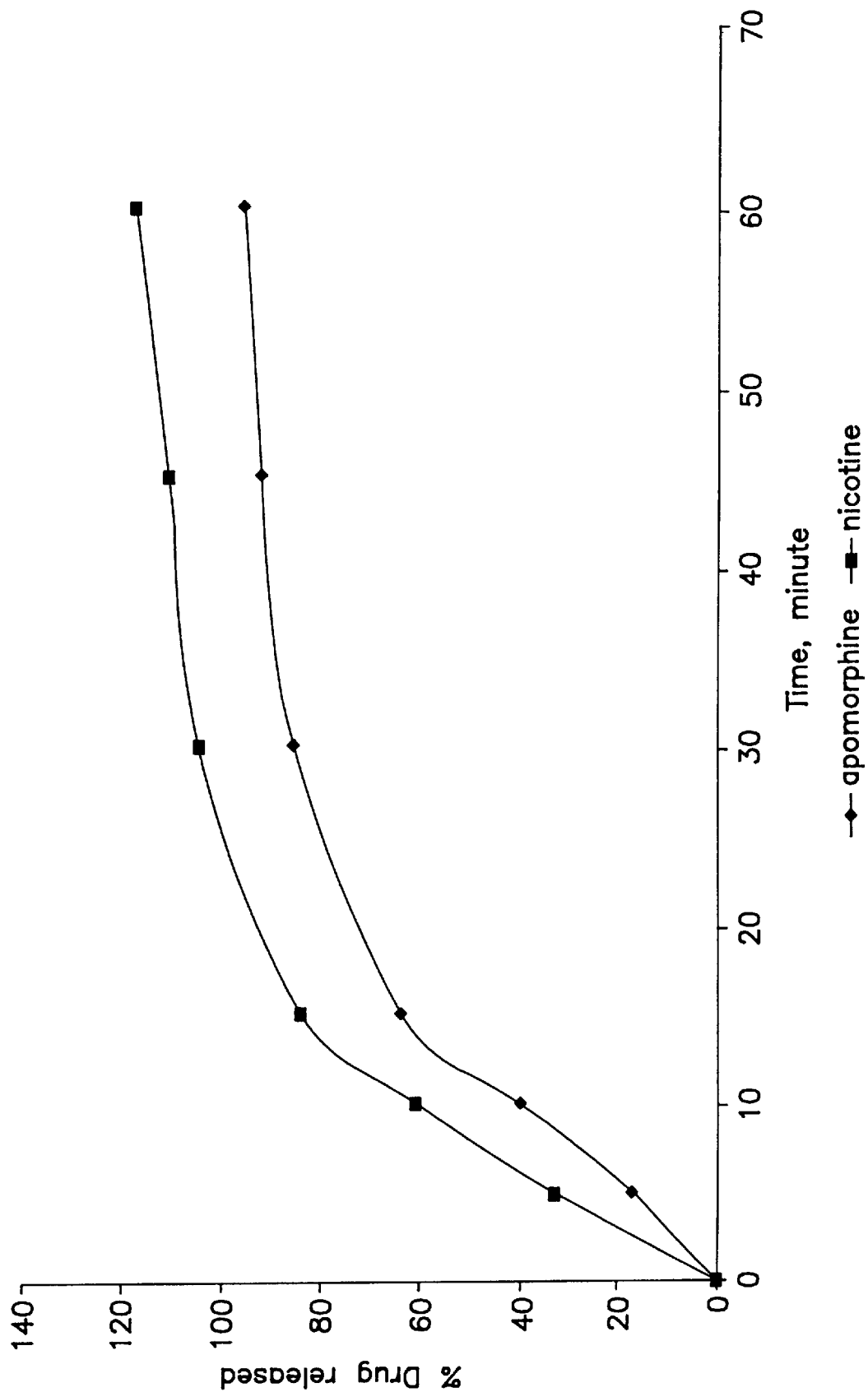
FIG. 7 is a graph of the dissolution pattern of apomorphine and the antiemetic agent nicotine for the layered tablets of Example 3.

Dissolution of apomorphine and nicotine for Composition C Tablets was measured and reported as described in Example 1. The results are presented in Table XXVI (below) and in FIG. 7. As expected, Composition C Tablets released nicotine from their outer layer relatively sooner and faster than the apomorphine from the core portion.

EXAMPLE 4
Apomorphine/Prochlorperazine Combination by Wet Granulation Technique—Composition D Composition D Tablets were prepared from the ingredients listed in Table XXIV (below). Each ingredient was weighed as indicated and passed through a #35 mesh screen (sieve opening of about 0.51 mm) to ensure granulation. A solution containing the apomorphine HCL, acesulfame-K, peppermint flavor, chocolate flavor, and citric acid was prepared by dissolving these ingredients into a mixture of equal volumes of distilled water and ethanol. The solution was mixed until clear, and then absorbed into the listed amount of microcrystalline cellulose (Avicel 302) by further mixing over a stainless steel pan at room temperature (20° C.) for about 30 minutes. The mixture was partially dried before granulating with a #60 mesh hand screen (sieve opening of about 0.25 mm).

TABLE XXIV

Apomorphine/Prochlorperazine Combination Tablet Composition

| Ingredient | mg/tablet |
|---|---|
| Apomorphine HCL | 4.0 |
| Prochlorperazine HCL | 5.0 |
| Acesulfame-K | 4.0 |
| Microcrystalline Cellulose | 37.5 |
| Peppermint flavor | 2.5 |
| Chocolate flavor | 2.0 |
| Citric acid | 3.0 |
| Hydroxypropylmethylcellulose | 10.0 |
| Mannitol | 68.0 |
| Sodium alginate | 10.0 |
| Magnesium stearate | 3.0 |
| TOTAL | 150.0 |

The resulting granules were dried at about 60° C. to 70° C. for about 2 hours. The dried granules were then mixed in a porcelain mortar and passed through a #35 mesh hand screen (sieve opening of about 0.51 mm).

All remaining ingredients listed in Table XXIV, except the magnesium stearate, were blended with the dry granules for about 5 minutes using a V-shaped blender. After 5 minutes of blending, magnesium stearate was added and the blending repeated for an additional 5 minutes. The resulting blend was compressed into tablets using the Stoke's tablet press fitted with 5/16" biconvex tooling.

Figure 8:
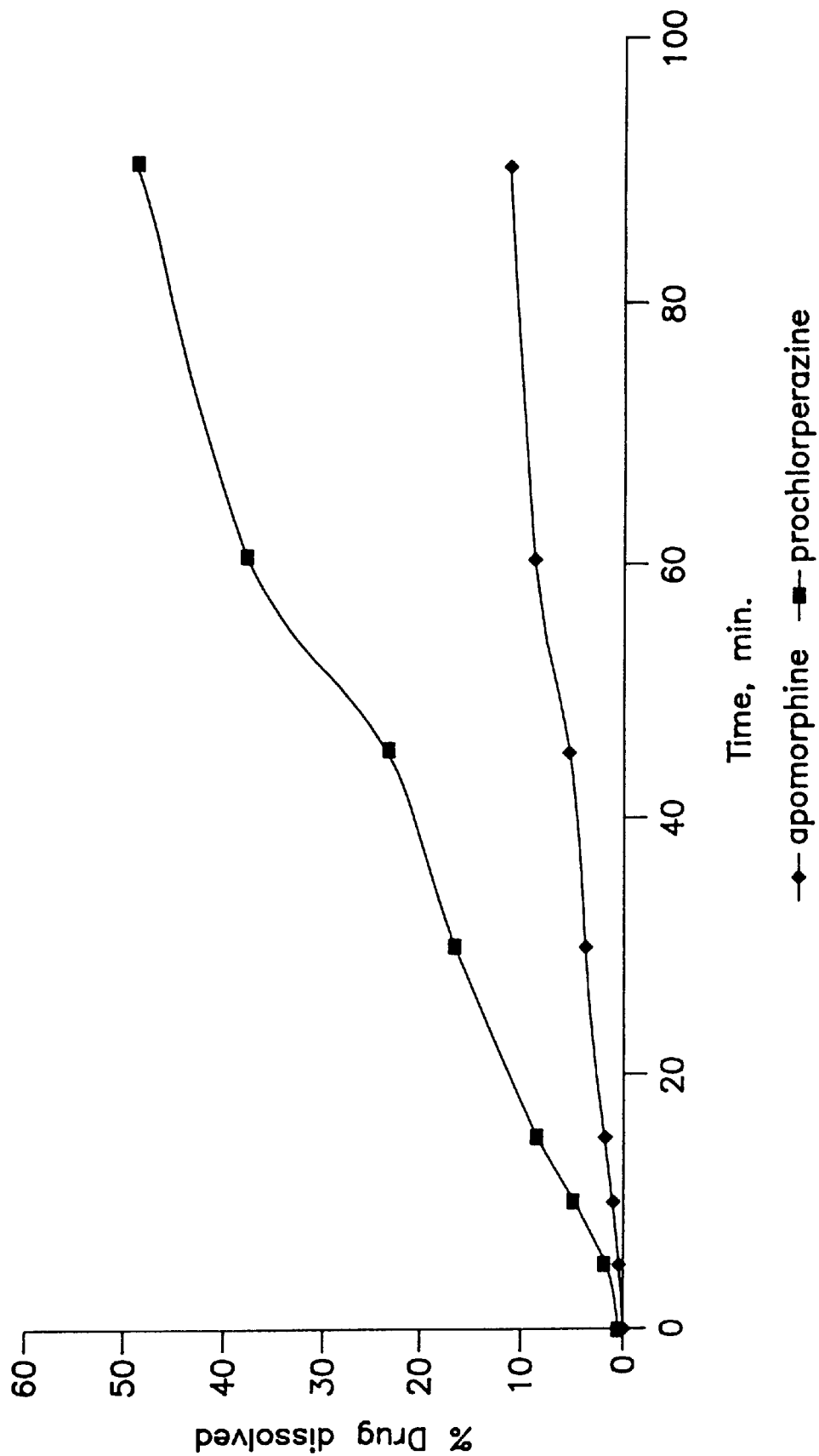
FIG. 8 is a graph of the dissolution pattern of apomorphine and the antiemetic agent prochlorperazine for the tablets of Example 4.

Composition D Tablets were evaluated as described for Example 1, except that absorbance was measured at 254 nm rather than 259 nm. The results are presented in Table XXVI (below) and in FIG. 8. Composition D Tablets released apomorphine relatively slower as compared to the release of prochlorperazine.

EXAMPLE 5
Apomorphine/Prochlorperazine Combination by Wet Granulation Technique—Composition E Composition E Tablets were prepared from the ingredients listed in Table XXIV (above). Each ingredient was weighed as indicated and passed through a #35 mesh screen (sieve opening of about 0.51 mm) to ensure granulation. Apomorphine HCL, the hydroxypropylmethyl cellulose, the sodium alginate, the citric acid, the acesulfame-K, the peppermint flavor, and the chocolate flavor were blended using 25 percent ethanol in deionized water. The resulting wet mass (Part A) was mixed in a porcelain mortar at room temperature (20° C.) for about 30 minutes, and then partially dried to obtain a single piece. The resulting mass was granulated using a #35 mesh hand screen (sieve opening of about 0.51 mm). The wet granules were dried at about 60° C. to 70° C. for about 1 to 1.5 hours, and periodically mixed during the drying stage. The resulting dried granules were then passed through a #35 mesh hand screen (sieve opening of about 0.51 mm).

Separately, prochlorperazine was added to and blended with the mannitol (Part B). Parts A and B were then combined and mixed for about 5 minutes in a V-shaped blender. Next, magnesium stearate was added to the blender, followed by continued blending for about 2 minutes.

The final mix was removed from the blender and compressed into tablets using a Stoke's single punch tablet press fitted with 5/16" diameter biconvex tooling. Tablets were prepared at various compressional forces, yielding tablets of different hardness.

Figure 9:
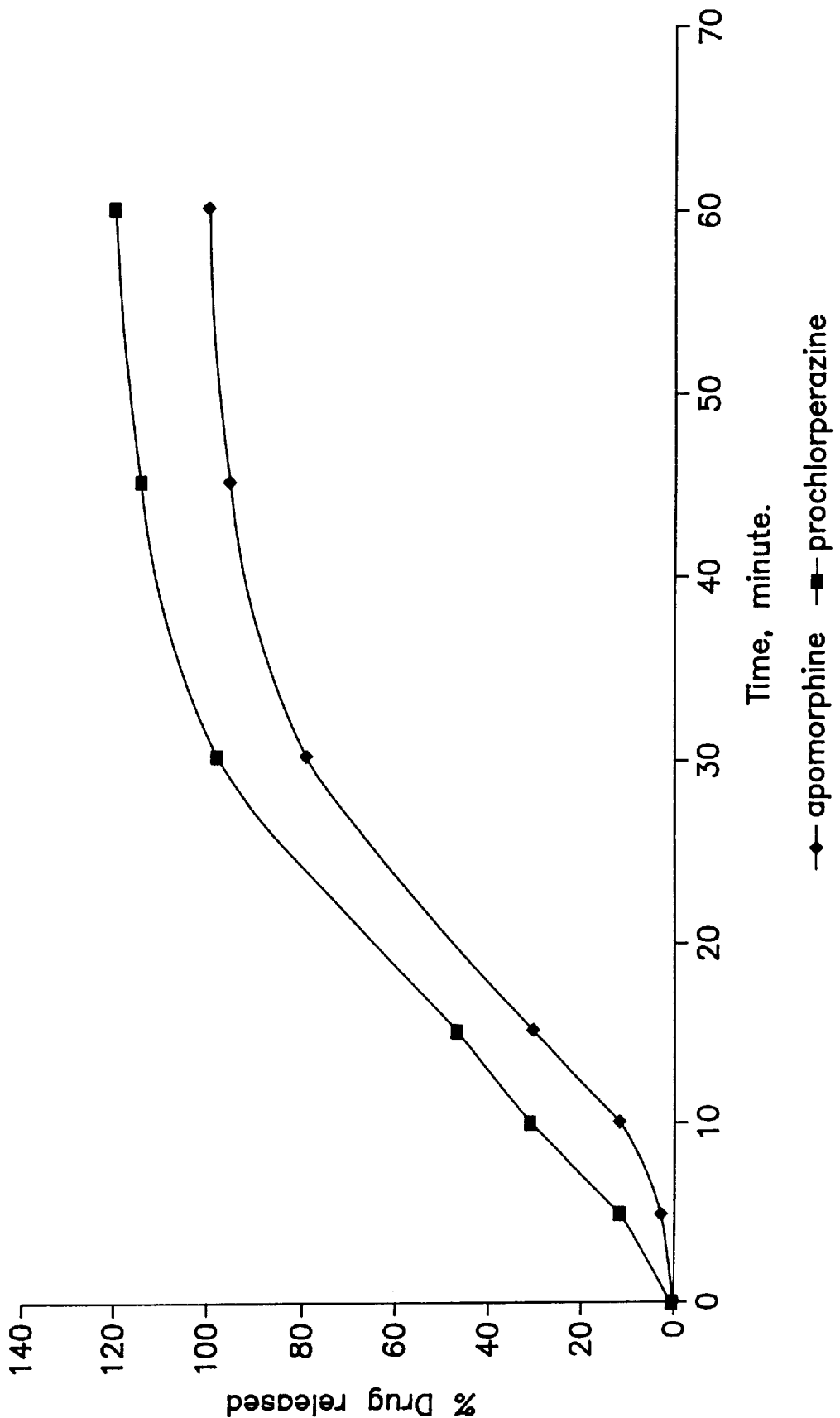
FIG. 9 is a graph of the dissolution pattern of apomorphine and the antiemetic agent prochlorperazine for the layered tablets of Example 5.

Dissolution of apomorphine and prochlorperazine for Composition E Tablets was measured and reported as described in Example 1. The results are presented in Table XXVI (below) and in FIG. 9. Composition E Tablets released apomorphine relatively slower as compared to the release of prochlorperazine.

EXAMPLE 6
Apomorphine/Prochlorperazine Layered Tablet Combination—Composition F Composition F Tablets were prepared according to the instructions presented in Example 3, except that the ingredients of Table XXV (below) were used. Prochlorperazine was substituted for nicotine and the sodium alginate was added in the same step as the hydroxypropylmethylcellulose.

TABLE XXV

Apomorphine/Prochlorperazine Layered Tablet Composition

| Ingredient | mg/tablet |
|---|---|
| Table core: | |
| Apomorphine HCL | 4.0 |
| Acesulfame-K | 1.6 |
| Microcrystalline Cellulose | 20.0 |
| Peppermint flavor | 1.0 |
| Chocolate flavor | 0.8 |
| Citric acid | 1.2 |
| Hydroxypropylmethylcellulose | 5.0 |
| Mannitol | 20.2 |
| Sodium alginate | 5.0 |
| Magnesium stearate | 1.2 |
| Tablet outer layer: | |
| Prochlorperazine | 5.0 |
| Acesulfame-K | 0.4 |
| Microcrystalline Cellulose | 35.6 |
| Mannitol | 46.0 |
| Magnesium stearate | 1.0 |
| Hydroxypropylmethylcellulose | 2.0 |
| TOTAL | 150.0 |

Figure 10:
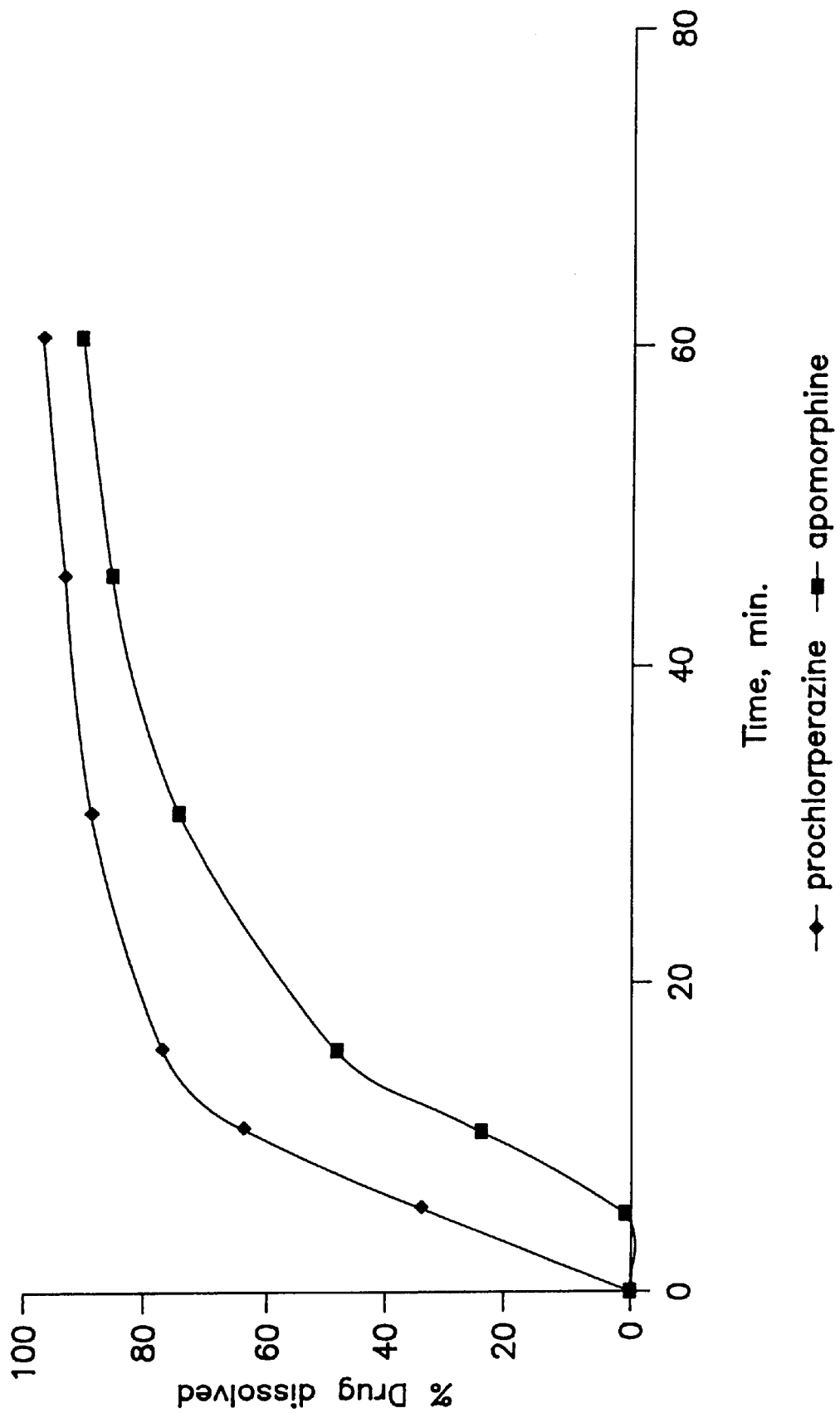
FIG. 10 is a graph of the dissolution pattern of apomorphine and the antiemetic agent prochlorperazine for the layered tablets of Example 6.

Composition F Tablets were evaluated as described for Example 1. The results are presented in Table XXVI (below) and in FIG. 10. Composition F Tablets released the antiemetic prochlorperazine relatively faster than the apomorphine, as expected.

EXAMPLE 7
Apomorphine/Prochlorperazine Layered Tablet Combination—Composition G The ingredients listed in Table XXV (above) were used to prepare a layered tablet having a core portion containing apomorphine HCL and an outer layer containing the antiemetic agent prochlorperazine. Each ingredient was weighed as indicated and passed through a #35 mesh screen (sieve opening of about 0.51 mm) to ensure granulation.

The core portion was prepared by dissolving the apomorphine HCL, acesulfame-K, peppermint flavor, chocolate flavor, and citric acid into a mixture of equal volumes of distilled water and ethanol. The solution was mixed until clear, and then absorbed into the listed amount of microcrystalline cellulose (Avicel 302) by further mixing over a stainless steel pan at room temperature (20° C.) for about 30 minutes. The mixture was partially dried before granulating with a #60 mesh hand screen.

The resulting granules were dried at about 60° C. to 70° C. for about 2 hours. The dried granules were then mixed in a porcelain mortar and passed through a #35 mesh hand screen (sieve opening of about 0.51 mm).

All remaining core ingredients listed in Table XXV, except the magnesium stearate, were blended with the dry granules for about 5 minutes using a V-shaped blender. After 5 minutes of blending, magnesium stearate was added and the blending repeated for an additional 2 minutes. The resulting blend was compressed into 60 mg tablet cores using the Stoke's tablet press fitted with 7/32" biconvex tooling.

The outer antiemetic layer was prepared by dissolving the prochlorperazine and acesulfame-K into a mixture of equal volumes of distilled water and ethanol. The solution was mixed until clear, and then absorbed into the listed amount of microcrystalline cellulose by mixing over a stainless steel pan at room temperature (20° C.) for about 30 minutes. The mixture was partially dried before granulating with a #60 mesh hand screen.

The resulting granules were dried at about 60° C. to 70° C. for about 2 hours, mixed in a porcelain mortar, and passed through a #35 mesh hand screen (sieve opening of about 0.51 mm). The mannitol and the hydroxypropylmethyl cellulose were blended with the dry outer-layer granules for about 5 minutes using a V-shaped blender. After 5 minutes of blending, magnesium stearate was added and the blending repeated for an additional 2 minutes.

Layered tablets were then prepared by compressing the outer-coating granules around tablet cores as described in Example 3.

Figure 11:
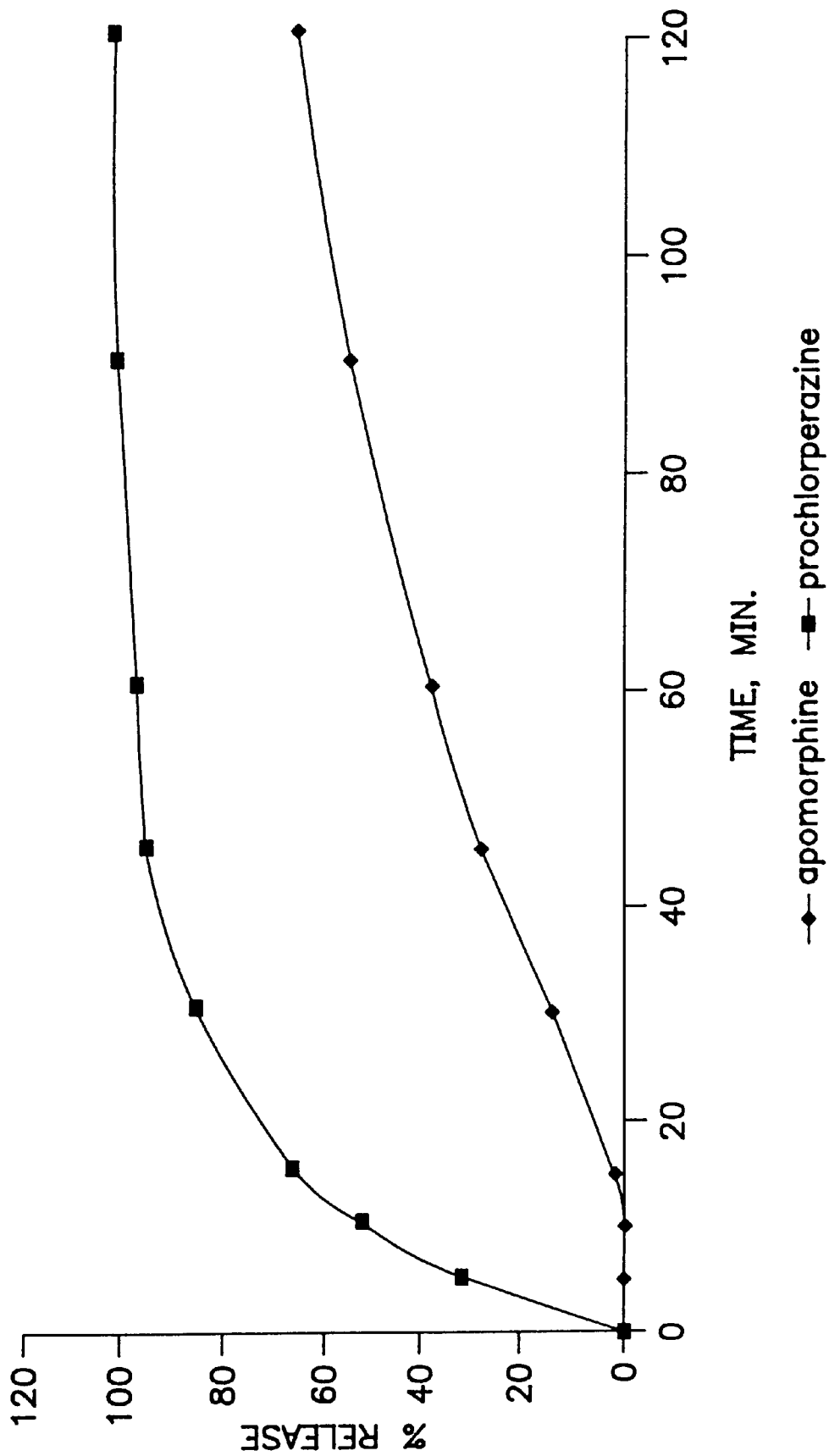
FIG. 11 is a graph of the dissolution pattern of apomorphine and the antiemetic agent prochlorperazine for the layered tablets of Example 7.

Dissolution of apomorphine and prochlorperazine for Composition G Tablets was measured and reported as described in Example 1. The results are presented in Table XXVI (below) and in FIG. 11. As expected, Composition G Tablets released prochlorperazine from their outer layer relatively sooner and faster than the apomorphine, which escapes from the core portion.

EXAMPLE 8
Comparison of Drug Release Profiles

Figure 12:
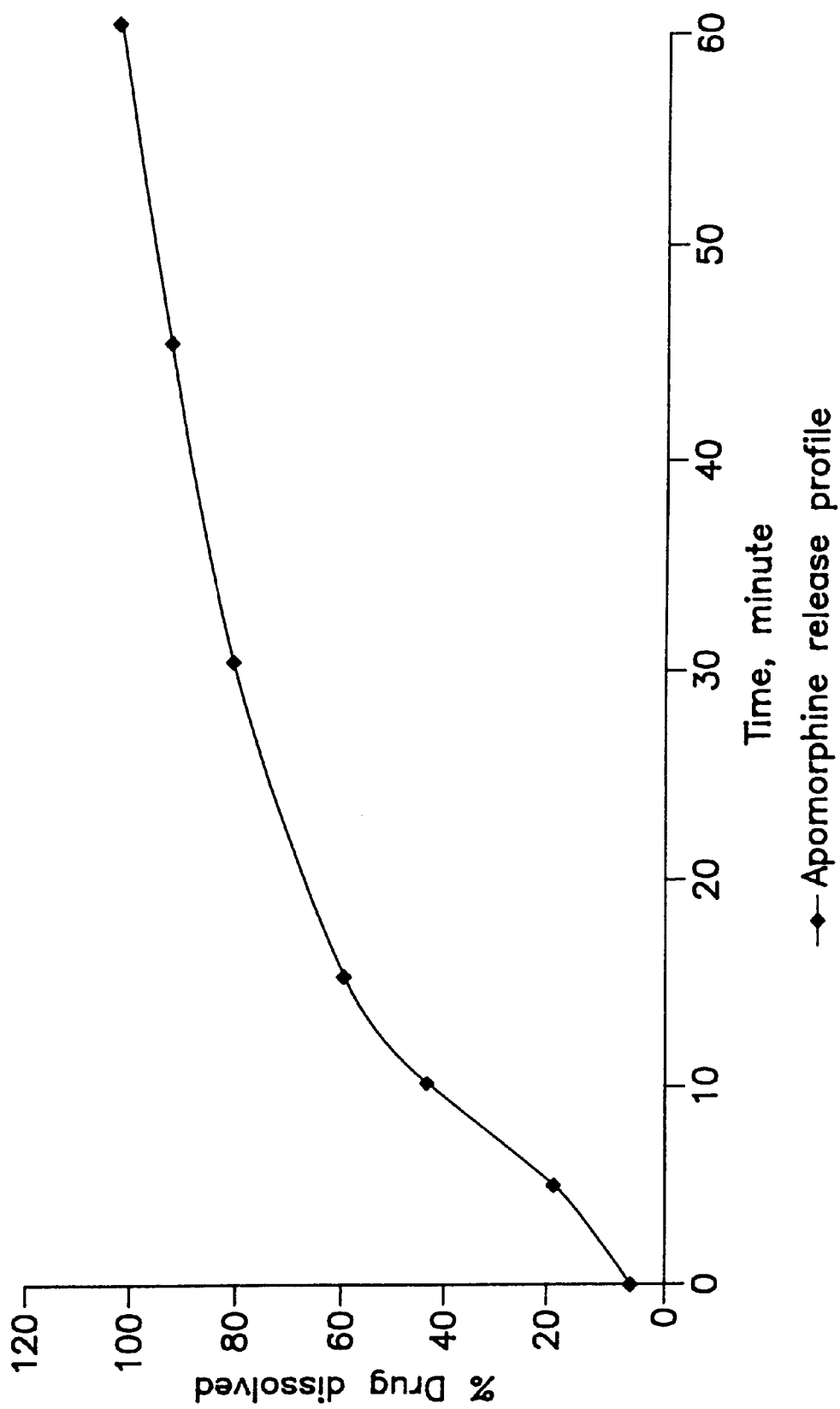
FIG. 12 is a graph of the dissolution of apomorphine for a sublingual apomorphine tablet as discussed in Example 8.

The dissolution profile of a commercially available soluble apomorphine HCl tablet (Apomorphine HCl, 6 mg of Apomorphine HCL in a 60 mg tablet) was analyzed as described for Example 1. The results of this test are shown graphically in FIG. 12, and listed in Table XXVI (below).

Also reported in Table XXVI are the time to 50 percent drug release ($T_{50}$), the time to 90 percent drug release ($T_{90}$), and the calculated dissolution constants of both the apomorphine and antiemetic agent (nicotine or prochlorperazine) for each example composition.

TABLE XXVI

Comparison Of Release Profiles And Tablet Hardness

| | Apomorphine HCL | | | Antiemetic Agent | | | | |
|---|---|---|---|---|---|---|---|---|
| Comp. | $T_{50}$ | $T_{90}$ | $K_{diss}$ | $T_{50}$ | $T_{90}$ | $K_{diss}$ | $r^2$ | Hardness, $k_p$ |
| A | 60 | 60 | 1.44 | 10 | 25 | 3.34 | 0.908 | 4.5 |
| B | 12 | 40 | 3.92 | 5 | 12 | 6.51 | 0.912 | 4.7 |

TABLE XXVI-continued

Comparison Of Release Profiles And Tablet Hardness

| | Apomorphine HCL | | | Antiemetic Agent | | | | |
|---|---|---|---|---|---|---|---|---|
| Comp. | $T_{50}$ | $T_{90}$ | $K_{diss}$ | $T_{50}$ | $T_{90}$ | $K_{diss}$ | $r^2$ | Hardness, $k_p$ |
| C | 13 | 45 | 4.29 | 8 | 20 | 5.66 | 0.899 | 2.5/4.9 |
| D | >90 | >90 | 0.13 | 90 | >90 | 0.54 | 0.945 | 6.5 |
| E | 22 | 40 | 2.76 | 16 | 27 | 3.16 | 0.944 | 4.2 |
| F | 15 | 60 | 3.42 | 7 | 30 | 5.29 | 0.956 | 2.5/4.8 |
| G | 80 | >120 | 0.67 | <10 | 40 | 2.68 | 0.932 | 3.5/5.5 |
| Soluable Apo Tablet | 13 | 30 | 3.82 | — | — | — | 0.909 | 4.2 |

These data demonstrate the ability of the present invention to release antiemetic agent relatively sooner and faster than the apomorphine. FIGS. 5 through 13 are graphs generated from the data presented in TABLE XXVI. Significantly, and well represented in graphical form, compositions according to the present invention also release apomorphine at an advantageously slower rate than that of the commercial sublingual table.

Figure 13:
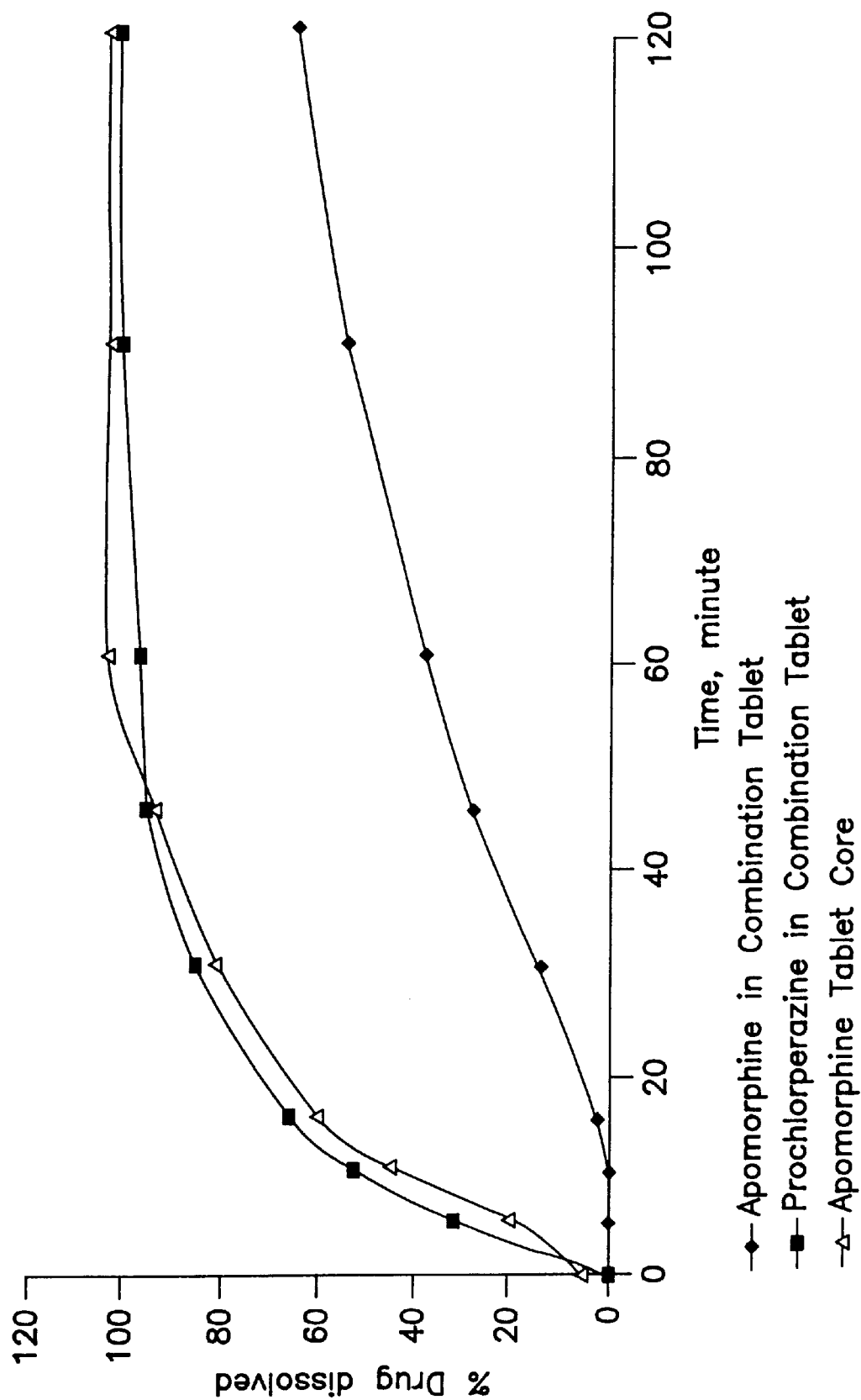
FIG. 13 is a graph comparing the dissolution pattern for the layered tablets of Example 7 with the dissolution of apomorphine for a commercially available soluble apomorphine tablet.

FIG. 13 is a composite graph of the dissolution profiles for a commercially available apomorphine soluble tablet and a Composition G Tablet (Example 7). This graph well demonstrates the advantage of a layered, staggered-release tablet according to the present invention.

The foregoing discussion, examples, and the reported studies are intended as illustrative of the present invention and are not to be taken as limiting. Still other variants within the spirit and scope of this invention are possible and will readily present themselves to those skilled in the art.

We claim:

1. A method suitable for treating erectile dysfunction in a male patient which comprises orally administering to the patient prior to sexual activity:
   an oral dosage of an antiemetic agent in an amount sufficient to substantially reduce nausea associated with use of apomorphine; and
   an oral dosage of apomorphine or a pharmaceutically acceptable acid addition salt thereof in an amount sufficient to induce and maintain an erection adequate for vaginal penetration.

2. The method in accordance with claim 1 wherein the antiemetic agent is a phenothiazine.

3. The method in accordance with claim 2 wherein the antiemetic agent is prochlorperazine.

4. The method in accordance with claim 1 wherein the antiemetic agent is a benzamide.

5. The method in accordance with claim 1 wherein the antiemetic agent is a meclizine.

6. The method in accordance with claim 1 wherein the antiemetic agent is a serotonin antagonist.

7. The method in accordance with claim 1 wherein the antiemetic agent is a member of the group consisting of hydroxyzine, dimenhydrinate, scopolamine, metopimazine, and diphenidol hydrochloride.

8. The method in accordance with claim 1 wherein the antiemetic agent is a ganglionic stimulating alkaloid and the apomorphine is administered to the patient as the hydrochloride salt.

9. The method in accordance with claim 8 wherein the antiemetic agent is nicotine sulfate and the weight ratio of apomorphine hydrochloride to nicotine sulfate administered to the patient is in the range of about 10 to about 1.

10. The method in accordance with claim 8 wherein the apomorphine and the antiemetic agent are co-administered to the patient in a single dosage unit comprising about 1 to about 10 milligrams apomorphine and about 0.5 to about 2 milligrams nicotine sulfate.

11. The method in accordance with claim 1 wherein the antiemetic agent is prochlorperazine hydrochloride.

12. The method in accordance with claim 11 wherein the weight ratio of apomorphine hydrochloride to prochlorperazine hydrochloride administered to the patient is in the range of about 5 to about 0.25.

13. The method in accordance with claim 11 wherein the amount of prochlorperazine hydrochloride administered to the patient is in the range of about 5 to about 150 micrograms per kilogram of patient's body weight.

14. The method in accordance with claim 1 wherein the apomorphine and the antiemetic agent are administered to the patient substantially concurrently.

15. The method in accordance with claim 1 wherein the apomorphine and the antiemetic agent are administered to the patient sequentially by first administering a composition comprising an antiemetic agent and thereafter a composition comprising apomorphine.

16. The method in accordance with claim 1 wherein the apomorphine and the antiemetic agent are co-administered to the patient as a sublingual tablet.

17. The method in accordance with claim 1 wherein the apomorphine is administered as a sublingual tablet and the antiemetic agent is administered as a buccal patch.

18. The method in accordance with claim 1 wherein apomorphine is administered to the patient as the hydrochloride salt.

19. An oral dosage unit comprising an antiemetic agent as a relatively faster release component and apomorphine as a component released after release of the antiemetic agent has begun.

20. The dosage unit of claim 19 in the form of a layered tablet.

21. The dosage unit of claim 19 wherein the antiemetic agent is a member of the group consisting of the phenothiazines, the benzamides, the meclizines, the serotonin antagonists, hydroxyzine, lobeline sulfate, dimenhydrinate, scopolamine, metopimazine, diphenidol hydrochloride, nicotine, and the acid addition salts thereof.

22. The dosage unit of claim 19 wherein the antiemetic agent is a prochlorperazine.

23. The dosage unit of claim 19 wherein the antiemetic agent is metoclopramide hydrochloride.

24. The dosage unit of claim 19 in the form of a tablet having a core portion containing the apomorphine and an outer layer portion containing the antiemetic agent.

25. The dosage unit of claim 19 having a time to 90 percent release of apomorphine in the range of about 25 minutes to about 300 minutes.

* * * * *